United States Patent
Gadhamshetty et al.

(10) Patent No.: US 10,388,977 B2
(45) Date of Patent: Aug. 20, 2019

(54) GENERATION OF ELECTRICITY AND OTHER VALUE-ADDED PRODUCTS FROM CULLED TOMATOES IN MICROBIALLY CATALYZED ELECTROCHEMICAL SYSTEMS

(71) Applicant: South Dakota Board of Regents, Pierre, SD (US)

(72) Inventors: Venkataramana Gadhamshetty, Rapid City, SD (US); Namita Shrestha, Rapid City, SD (US); Alex Fogg, Fort Myers, FL (US)

(73) Assignees: SOUTH DAKOTA BOARD OF REGENTS, Pierre, SD (US); FLORIDA GULF COAST UNIVERSITY BOARD OS TRUSTEES, Fort Myers, FL (US)

( * ) Notice: Subject to any disclaimer, the term of this patent is extended or adjusted under 35 U.S.C. 154(b) by 133 days.

(21) Appl. No.: 15/476,768

(22) Filed: Mar. 31, 2017

(65) Prior Publication Data
US 2017/0288252 A1   Oct. 5, 2017

Related U.S. Application Data

(60) Provisional application No. 62/315,709, filed on Mar. 31, 2016.

(51) Int. Cl.
*H01M 8/16* (2006.01)
*C02F 1/469* (2006.01)
(Continued)

(52) U.S. Cl.
CPC ............ *H01M 8/16* (2013.01); *C02F 1/4604* (2013.01); *C02F 1/4691* (2013.01); *C12M 29/00* (2013.01);
(Continued)

(58) Field of Classification Search
CPC ....... H01M 8/16; C02F 1/4604; C02F 1/4691; C02F 2103/08; C12M 29/00;
(Continued)

(56) References Cited

U.S. PATENT DOCUMENTS

2007/0259216 A1* 11/2007 Logan ................. H01M 4/8605
429/2
2009/0017512 A1*  1/2009 May ....................... C12M 21/12
435/165

(Continued)

FOREIGN PATENT DOCUMENTS

CN           103482728 A   *  1/2014

OTHER PUBLICATIONS

Gadhamshetty et al.; "Evaluation of Laminaria-based microbial fuel cells (LbMs) for electricity production"; Bioresource Technology 127 (available online Sep. 29, 2012), pp. 378-385. (Year: 2012).*

(Continued)

*Primary Examiner* — Gregg Cantelmo
(74) *Attorney, Agent, or Firm* — Goodhue, Coleman & Owens, P.C.

(57) ABSTRACT

The United States faces significant environmental burden to treat and transport ~0.61 billion kg of defective tomatoes (culled tomatoes) every year. The present disclosure provides for the treatment and processing of culled tomatoes in microbial-electrochemical systems, using the microbial fuel cell as a model reactor. The fundamental differences between the long-term oxidative behavior of unprocessed culled tomatoes compared to the three readily soluble substrates (dextrose, acetate, and wastewater) are disclosed. AC electrochemical impedance spectroscopy (EIS) analyses indicate the influential impedance contributions of the peel & seed to the cull oxidation. Cyclic voltammetry tests indicate that the indigenous redox-active pigments in the (Continued)

cull influence the faradaic processes involved in the cull oxidation.

16 Claims, 14 Drawing Sheets

(51) Int. Cl.
    C02F 1/46    (2006.01)
    C12M 1/00    (2006.01)
    C12M 1/34    (2006.01)
    C12N 1/20    (2006.01)
    C02F 103/08    (2006.01)

(52) U.S. Cl.
    CPC ............ *C12M 41/28* (2013.01); *C12M 43/00* (2013.01); *C12M 43/08* (2013.01); *C12N 1/20* (2013.01); *C02F 2103/08* (2013.01); *Y02E 60/527* (2013.01)

(58) Field of Classification Search
    CPC ...... C12M 41/28; C12M 43/00; C12M 43/08; C12N 1/20; Y02E 60/527
    See application file for complete search history.

(56) References Cited

U.S. PATENT DOCUMENTS

2010/0270158 A1* 10/2010 Logan ................ C02F 1/469
    204/522
2011/0281139 A1* 11/2011 Huang .................. B01D 61/44
    429/2

OTHER PUBLICATIONS

Logan et al.; "Electricity-producing bacterial communities in microbial fuel cells"; Trends in Microbiology, vol. 14, No. 12, (available online Oct. 16, 2006); pp. 512-518. (Year: 2006).*

Leong et al.; "Ion exchange membranes as separators in microbial fuel cells for bioenergy conversion: A comprehensive review"; Renewable and Sustainable Energy Reviews 28 (available online Sep. 3, 2013); pp. 575-587. (Year: 2013).*

Bartz et. al., "Chlorine Concentration and the Inoculation of Tomato Fruit in Packinghouse Dump Tanks", The American Phytopathological Society (Aug. 2001), Plant Disease 85 pp. 885-889.

Batstone et. al. "The IWA Anaerobic Digestion Model No. 1 (ADM1)", Water Science and Technology vol. 45(10) pp. 65-73 (2002).

Boltz "The Kinetics of Particulate Substrate Utilization by Bacterial Films", University of New Orleans Theses and Dissertations pp. 254 (May 2005).

Borole et. al., "Enhancement in current density and energy conversion efficiency of 3-dimensional MFC anodes using pre-enriched consortium and continuous supply of electron donors", www.elsevier.com/locate/biortech, Bioresource Technology 102 pp. 5098-2104 (Jan. 25, 2011).

Calabro' et al., "Anaerobic Digestion of Tomato Processing Waste: Effect of Alkaline Pretreatment", Proceedings of the 14th International Conference on Environmental Science and Technology Rhodes, Greece, Sep. 3-5, 2015.

Cammack et. al., "Midpoint Redox Potentials of Plant and Algal Ferredoxins", Biochem. J. 168 pp. 205-209 (Apr. 1977).

Cardenas-Robles et. al., "Development of an activated carbon-packed microbial bioelectrochemical system for azo dye degradation", "journal homepage: www.elsevier.com/locate/biortech", Bioresource Technology 127 pp. 37-43 (Sep. 27, 2013).

Chae et. al., "Effect of different substrates on the performanace, bacterial diversity, and bacterial viability in microbial fuel cells", "www.elsevier.com/locate/biortech", Bioresource Technology 100 pp. 3518-3525 (Apr. 3, 2009).

Chahal et. al., "Effect of Tomato Packinghouse Wastewater Properties on Phosphorus and Cation Leaching in a Spodosol", Journal of environmental quality 40(3) pp. 999-1009 (May 2011).

Chandrashekhar et. al. "Solid phase bio-electrofermentation of food waste to harvest value-added products associated with waste remediation", www.elsevier.com/locate/wasman, Waste Management vol. 45 pp. 57-65 (2015).

Choi et. al, "Optimal biofilm formation and power generation in a micro-sized microbial fuel cell (MFC)", www.elsevier.com/locate/sna, Sensors and Actuators A 195 pp. 206-212 (2013).

Cusick et. al, "Phosphate recovery as struvite within a sinlge chamber microbial electrolysis cell", www.elsevier.com/locate/biortech, Bioresource Technology 107 pp. 110-115 (2012).

Cusick et. al., "Performance of a pilot-scale continuous flow microbial electrolysis cell fed winery wastewate", Appl Microbiol Biotechnol 89 pp. 2053-2063 (2011).

Danaee et. al., "Impedance spectroscopy analysis of glucose electrooxidation on Ni-modified glassy carbon electrode", www.elsevier.com/locate/electacta, Electrochimicia Acta 53 pp. 6602-6609 (Apr. 22, 2008).

Dole, "A Relation Between Non-Esterified Fatty Acids in Plasma and the Metabolism of Glucose", The Rockefeller Institute for Medical Research, New York City, N.Y. (Aug. 17, 1995), pp. 150-154.

Fangzhou et. al., "Electricity generation directly using human feces wastewater for life support system", "www.elsevier.com/locate/actaastro", Acta Astronautica 28 pp. 1537-1547 (Feb. 18, 2010).

Fernandez-Gomez: "Continuous-feeding vermicomposting as a recycling management method to revalue tomato-fruit wastes from green house crops", "journal homepage: www.elsevier.com/locate/wasman", Waste Management 30 pp. 2461-2468 (Aug. 2, 2010).

Fogg et. al., "Can a microbial fuel cell resist the oxidation of Tomato pomace?", journal homepage: www.elsevier.com/locate/jpowsour, Journal of Power Sources 279 pp. 781-790 (Jan. 6, 2015).

Fornes et. al., "Composing versus vermicomposting: A comparative study of organic matter evolution through straight and combined processes", journal homepage: www.elsevier.com/locate/biortech, Bioresource Technology 118 pp. 296-305 (May 17, 2012).

Fricke et. al., "On the use of cyclic voltammetry for the study of anodic electron transfer in microbial fuel cells", Energy & Environmental Science 1(1) pp. 144-147 (Mar. 18, 2008).

Gadhamshetty et. al., "Dark and acidic conditions for fermentative hydrogen production", "Journal homepage: www.elsevier.com/locate/he", International Journal of Hydrogen Energy 34 pp. 821-826 (Dec. 17, 2008).

Gadhamshetty et. al., "Evaluation of Laminaria-based microbial fuel cells (LbMs) for electricity production", www.elsevier.com/locate/biortech, Bioresource Technology 127 pp. 378-385 (Sep. 29, 2012).

Gadhamshetty et. al., "Modeling dark fermentation for biohydrogen production: ADM1-based model vs. Gompertz model", www.elsevier.com/locate/he, International Journal of Hydrogen Energy 35 pp. 479-490 (2010).

Gadhamshetty et. al., "Nano-engineered biocatalyst-electrode structures for next generation microbial fuel cells", www.elsevier.com/locate/nanoenergy, Nano Energy 1 pages 3-5 (2012).

Ge et. al., "Long-term investigation of microbial fuel cells treating primary sludge or digested sludge", www.elsevier.com/locate/biortech, Bioresource Technology 136 pp. 509-514 (Mar. 13, 2013).

Gustafson: "Distribution of Thiamin and Riboflavin in the Tomato Plant", Plant physiology 22(4) pp. 620-626, (Mar. 30, 1947).

Haque et. al., "Characteristics of electricity production by metallic and nonmetallic anodes immersed in mud sediment using sediment microbial fuel cell", Materials Science and Engineering 88 (2015), pp. 1745-1753.

Ieropoulos et. al. "Waste to real energy: the first MFC powered mobile phone", Phys. Chem. Chem. Phys. vol. 15 (37) pp. 15312-15316 (2013).

Logan et. al., "Assessment of Microbial Fuel Cell Configurations and Power Densities", Journal: Environmental Science & Technology Letters, American Chemical Society (Jul. 28, 2015), pp. 1-22.

(56) References Cited

OTHER PUBLICATIONS

Magnuson et. al., "Isolation, characterization and gene sequence analysis of membrane-associated 89 kDa Fe (III) reducting cytochrome c from Geobacter sulfurreducens", Biochem. J 359 pp. 147-152 (2001).

Mink et. al., "Energy harvesting from organic liquids in micro-sized microbial fuel cells", NPG Asia Materials 6(3), e89 (2014).

Monnet, "An Introduction to Anaerobic Digestion of Organic Wastes, Remade Scotland", (Nov. 2003), pp. 1-48.

Ramasamy et. al., "Impedence Spectroscopy as a Tool for Non-Intrusive Detection of Extracellular Mediators in Microbial Fuel Cells", Biotechnol Bioeng 104(5) pp. 882-891.

Ribaudo et. al., "Land application of manure by animal feeding operations: Is more land needed?", Journal of Soil and Water Conservation pp. 30-38 (2003).

Riggi et. al., "Fresh tomato packinghouses waste as high added-value biosource", www.elsevier.com/locate/resconrec, Resources, Conservation and Recycling 53 pp. 96-106 (Nov. 2, 2008).

Sa' et. al., "Sugars Electrooxidation at Glassy Carbon Electrode Decorate with Multi-Walled Carbon Nanotubes with Nickel Oxy-Hydroxide", Int. J. Electrochem. Sci., 9 pp. 7746-7762 (2014).

Sheets et. al., "Beyond land application: Emerging technologies for the treatment and reuse of anaerobically digested agricultural and food waste", journal homepage: www.elsevier.com/locate/wasman, Waste Management 44 pp. 94-115, (Jul. 30, 2015).

Shehab et. al., "Enhanced water desalination efficiency in an air-cathode stacked microbial electrodeionization cell (SMEDIC)", www.elsevier.com/locate/memsci, Journal of Membrance Science 469 pp. 364-370 (Jul. 8, 2014).

Smith et. al. "Redox Properties of Several Bacterial Ferredoxins Using Square Wave Voltammetry", The Journal of Biological Chemistry vol. 265(24) pp. 14371-14376 (Aug. 25, 1990).

Song et. al., "Influence of biomass addition on electricity harvesting from solid phase microbial fuel cells", www.elsevier.com/locate/he, International Journal of Hydrogen Energy 39 pp. 1056-1062 (Nov. 17, 2015).

Sydney et. al., "Economic process to produce biohydrogen and volatile fatty acids by a mixed culture using vinasse from sugarcane ethanol industry as nutrient source", "journal homepage: www.elsevier.com/locate/biortech", Bioresource Technology 195 pp. 380-386 (Feb. 20, 2014).

Teo et. al., "Enzyme augmentation of an anaerobic membrane bioreactor treating sewage containing organic particulates", www.elsevier.com/locate/watres, Water Research 48 pp. 335-344 (Oct. 3, 2013).

Toor et. al. "Solutions for Managing Tomato Culls in Florida Tomato Packinghouses", One of a series of the Soil and Water Science Department, UF/IFAS Extension, University of Florida (Aug. 2012).

Torres et. al., "Selecting Anode-Respiring Bacteria Based on Anode Potential: Phylogenentic, Electrochemical, and Microscopic Characterization", Environ. Sci. Technol. 43 pp. 9519-9524 (2009).

USDA: "United States Standards for Grades of Tomatoes for Processing", http://www.ers.usda.gov/datafiles/Vegetable_and_Pulses_Yearbook_Tables/SandU-Fresh%20Market/YRBK2015_Section%202_SandU%20Fresh.xlsx (2014).

Wang et al., "A comprehensive review of microbial electrochemical systems as platform technology", "www.elsevier.com/locate/biotechadv", Biotechnology Advances 31 (2013), pp. 1796-1807.

Wang et. al., "Electrical analysis of compost solid phase microbial fuel cell", "www.elsevier.com/locate/he", International Journal of Hydrogen Energy 38 pp. 11124-11130 (Apr. 10, 2013).

Wu et. al., "Anode-biofilm electron transfer behavior and waste-water treatment under different operational modes of bioelectrochemical system", "www.elsevier.com/locate/biortech", Bioresource Teachnology 157 pp. 305-309 (Feb. 2014).

Xiao et. al., "Evaluation of normalized energy receovery (NER) in microbial fuel cells affected by reactor dimensions and substrates", www.elsevier.com/locate/biortech, Bioresource Technology 157 pp. 77-83 (2014).

Zhang et. al., "Photoelectrochemical reforming of biomass for hydrogen generation", RSC Advances 4(70), pp. 37395-37399 (2014).

\* cited by examiner

GENERATION OF ELECTRICITY AND OTHER VALUE-ADDED PRODUCTS FROM CULLED TOMATOES IN MICROBIALLY CATALYZED ELECTROCHEMICAL SYSTEMS

CROSS-REFERENCE TO RELATED APPLICATIONS

This application claims priority under 35 U.S.C. § 119 to provisional application Ser. No. 62/315,709 filed Mar. 31, 2016, which is incorporated by reference in its entirety.

GRANT REFERENCE

This disclosure was made with government support under #1454102 and #NNX13AB25A awarded by the NSF and NASA, respectively. The government has certain rights in the disclosure.

BACKGROUND

I. Field of the Disclosure

Methods and systems for treating culled tomatoes in microbial-electrochemical systems (MESs) are disclosed where MES can refer to groups of microbial fuel cell, microbial desalination cell, and microbial capacitive deionization cell; all of the cells require the oxidation power in the anode to complete the circuit. Specifically, but not exclusively, a microbial fuel cell (referencing a living cell such as bacteria) is used as the model for MES and the chemical energy in culled tomatoes is used to generate oxidation current that is subsequently converted into DC electric power. Methods and systems for treating culled tomatoes containing a variety of redox-active mediators such as carotenoids, kampferol, malvin, myricetin, naringenin, naringin, petunidin, quercetin, and riboflavin in MESs are also disclosed. Further methods and systems disclose redox-active mediators catalyzing extracellular electron transfer from anode-respiring bacteria to solid electrodes in MESs.

II. Description of the Prior Art

Conventional biotechnologies are not designed to optimize energy production from culled tomatoes. Activated sludge processes are suited to diluted wastewater (WW); however, they also require significant energy inputs. Moreover, the land application of culls is not an attractive option due to ever-increasing stringent regulations. On-site composting requires expensive equipment during site preparation, demands lengthy treatment periods, and poses odor and dust issues. Anaerobic digestion (AD) is an established technology for generating methane-rich biogas but requires a purification step to recover methane. Dark fermentation generates hydrogen-rich biogas, but requires a purification step for separating hydrogen. Therefore a need in the art exists that focuses on the impedance to the oxidation of the particulate organic matter from culled tomatoes.

SUMMARY

Cyclic voltammetry (CV) tests confirm the electrochemical influence of mediators such as carotenoids, flavanoids and quercetins on oxidation of culled tomatoes in MESs.

According to at least one exemplary aspect, culled tomatoes containing a variety of redox-active species such as carotenoids, kampferol, malvin, myricetin, naringenin, naringin, petunidin, quercetin, and riboflavin qualifying as redox-active mediators in MESs are disclosed.

According to at least one other exemplary aspect, redox-active mediators in MESs are characterized with: i) fast redox equilibration; ii) fully reversible reactions; iii) experimentally established standard redox potentials; and iv) defined stoichiometry with respect to number of electron and protons during faradaic processes.

According to another exemplary aspect, disclosed mediators catalyze extracellular electron transfer from anode-respiring bacteria to solid electrodes in MESs and enhance their performance.

According to yet another exemplary aspect, strategies for mixing culled tomatoes with dilute wastewaters (e.g., municipal wastewater) and using the mixture to drive the MESs and particularly to generate electricity in MFCs is disclosed.

According to at least one other exemplary aspect, a method for generating electricity from tomato matter, a system for generating electricity from tomatoes, and a process for generating electrical current from tomato matter is disclosed. In a preferred form, the tomatoes and tomato matter of the method, process and system comprises tissue, columella, pericarp, vascular bundle, and locular cavity, and in at least one instance comprises tomato peel and tomato seed.

According to another exemplary aspect, impedance contributions of the peel & seed to the cull oxidation are disclosed. In a preferred aspect, the indigenous redox-active pigments in the cull influence the faradaic processes involved in cull oxidation. In another preferred aspect, pomace oxidation associated with a redox-active mediator undergoes a quasi-reversible reaction at higher potential ($E_p=0$ V vs Ag/Agcl), wherein charge transfer impedance appears as a distinct time constant in the mid-frequency region.

According to one exemplary embodiment, a method for generating electricity from matter derived from a tomato is disclosed. A microbial electrochemical system is provided having a bioreactor with opposing electrodes connected to electrical circuitry and separated by a membrane layer. The bioreactor has a flow pathway, an inlet and an outlet passing between the opposing electrodes. Tomato matter is introduced into the flow pathway of the microbial electrochemical system. The tomato matter contains an anode-respiring bacteria. Extracellular electron transfer is catalyzed from the anode-respiring bacteria of the tomato matter into the opposing electrodes in the microbial electrochemical system.

According to another exemplary embodiment, a microbial electrochemical system for generating electricity from matter derived from a tomato is disclosed. The system includes a bioreactor with opposing electrodes connected to electrical circuitry and separated by a membrane layer. The bioreactor has a flow pathway, an inlet and an outlet passing between the opposing electrodes. The tomato matter contains an anode-respiring bacteria that is introduced into the flow pathway of the microbial electrochemical system. Extracellular electron transfer is catalyzed from the anode-respiring bacteria of the tomato matter into the opposing electrodes in the microbial electrochemical system for generating electricity.

According to another exemplary embodiment, a galvanic process for using chemical energy from tomato matter is disclosed. The galvanic process includes a microbial electrochemical device with electrical circuitry, wherein the microbial electrochemical device has a flow pathway, an inlet and an outlet passing there-through. One or more controls operably configured with the electrical circuitry to ascertain one or more outputs for polarization, impedance and voltammetry of the microbial electrochemical device. The tomato matter contains an anode-respiring bacteria that is introduced into the flow pathway of the microbial electrochemical device. Extracellular electron transfer is catalyzed from the anode-respiring bacteria of the tomato matter by the microbial electrochemical device. In a preferred form, the microbial electrochemical device is a microbial desalination cell for using the chemical energy of the tomato matter to desalinate sea water. In another preferred form, the microbial electrochemical device is a microbial capacitive deionization cell for using the chemical energy of the tomato matter to deionize brackish water.

One or more of these and/or other objects, features, or advantages of the present invention will become apparent from the specification and claims that follow. No single embodiment need provide each and every object, feature, or advantage. Different embodiments may have different objects, features, or advantages. Therefore, the present invention is not to be limited to or by an object, feature, or advantage stated herein.

BRIEF DESCRIPTION OF THE DRAWINGS

Illustrated embodiments of the disclosure are described in detail below with reference to the attached drawing figures, which are incorporated by reference herein, and where.

BRIEF DESCRIPTION OF THE TABLES

Illustrated embodiments of the disclosure are described in detail below with reference to the attached Tables, which are incorporated by reference herein, and where:

Table 1 provides a tabulated representation of constituents of tomato waste and their role in microbial electrochemical systems in accordance with illustrative aspects of the present disclosure;

Table 2 provides a tabulated representation for test and control details for MGCs in accordance with illustrative aspects of the present disclosure;

Table 3 provides a tabulated representation for some experimental results in accordance with illustrative aspects of the present disclosure;

Table 4 provides a tabulated representation of results for a one-way ANOVA test for open circuit voltage values in peel & seed, cull, and dextrose in accordance with illustrative aspects of the present disclosure; and Table 5 provides a tabulated representation of statistics for a one-way ANOVA test for open circuit voltage values in peel & seed, cull, and dextrose in accordance with illustrative aspects of the present disclosure.

DETAILED DESCRIPTION

1. Introduction

Figure 7:
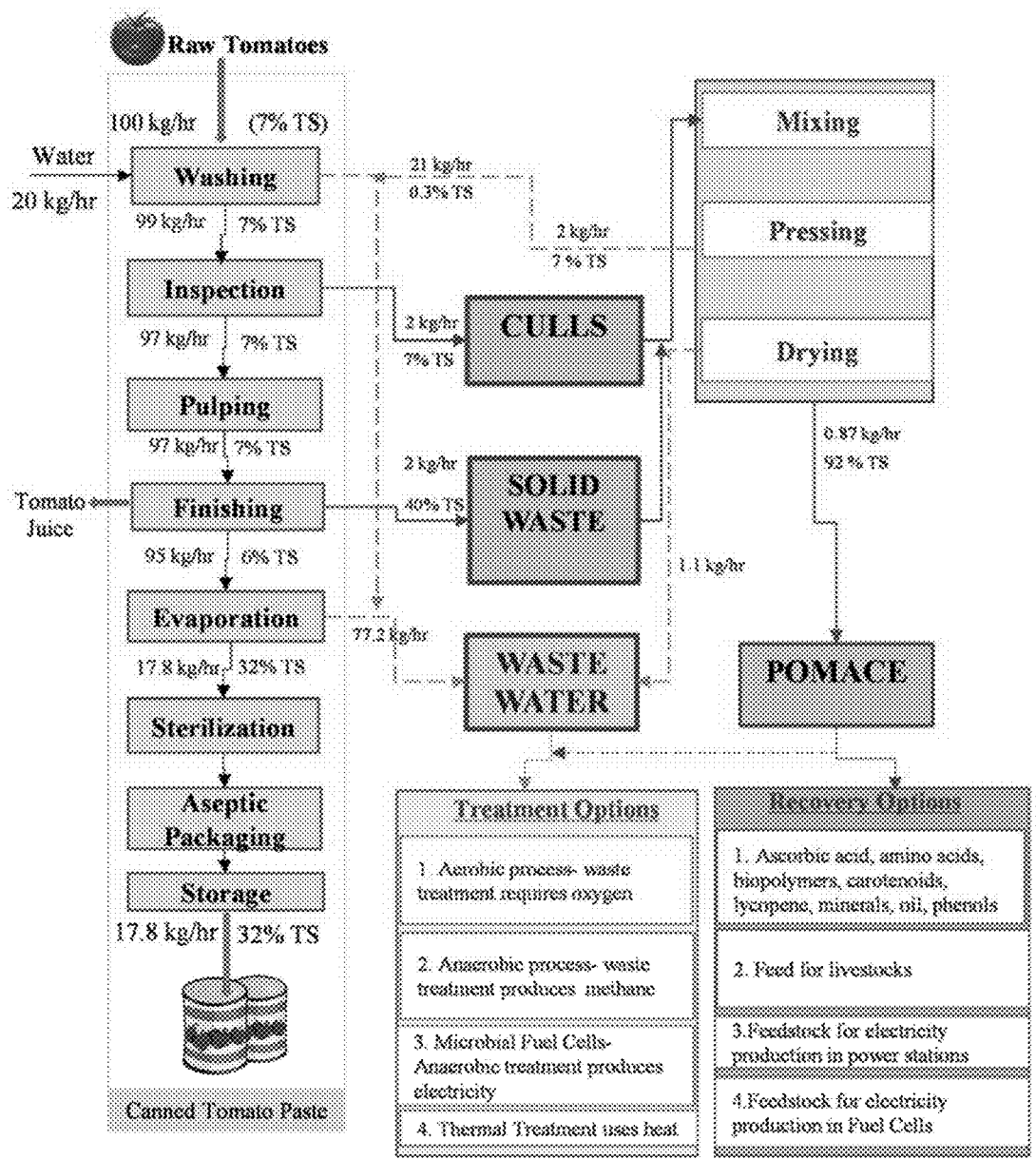
FIG. 7 provides a pictorial schematic of a tomato processing plant for the production of canned tomato paste in accordance with illustrative aspects of the present disclosure.

Tomato packinghouses in the U.S generate 6.12×108 kg of defective tomatoes (culled tomatoes) every year. Tomatoes are deemed defective when they fail customer requirements for firmness and color due to freezing traces and growth cracks; they have a stem over 3 inches of length, anthracnose, mold, decay, gray wall, or virus mottling; and they have cloudy spots, ghost spots, internal browning and sunscalds. With U.S. tomato production reaching as high as 1.53×109 kg/year (~81% production in CA, Al, FL, GA, NC, SC, TN, and VA), the packaging houses incur significant disposal costs. Similarly, processing plants generate culled tomatoes during washing, inspection, pulping, juice finishing, evaporation, sterilization, packing, and storage (FIG. 7). A kilogram of processed tomatoes generates 20 grams of culled tomatoes and 20 grams of peel and skin residues (FIG. 7). The packaging houses often prefer to hire third-party vendors to dispose of the culled tomatoes, incurring significant transportation costs. Moreover, regarding FIG. 7, a kilogram (kg) of a processed tomato generates 0.02 kg of culled tomatoes (7% total solids), 0.02 kg of miscellaneous solid organic waste (40% total solids), and 77 kg of wastewater. The culled tomatoes and miscellaneous solid wastes can be processed for commercial use. However, the disposal of as is culled tomatoes, pomace, and other solids wastes requires expensive treatment options.

The available biotechnologies are not designed to optimize the energy production from the solid organic wastes such as culled tomatoes. Activated sludge processes are more suitable for the dilute wastewater (WW) and require energy inputs (~112 KW per million gallons of WW). The land application of culled tomatoes may not be an attractive option due to ever-increasing stringent regulations. On-site composting requires expensive equipment during the site preparation demands lengthy treatment periods and poses both odor and dust issues. Anaerobic digestion (AD) is an established technology for generating methane-rich biogas but it requires purification step to recover methane. Dark fermentation can also be used to generate hydrogen-rich biogas, but it also can require purification.

TABLE 1

Various constituents of tomato waste and their role in the anode of MFCs.

| Defective Tomatoes | Nutrition Elements | Role in microbial electrochemical systems |
|---|---|---|
| Cull | Sucrose | Electron donor ($\Delta G^0 f = -1{,}551.85$ KJ/mole) |
| Peel | Amino Acids | Electron donor ($\Delta G^0 f = -763$ KJ/mole) |
| Seed | Oleic Acid | Electron donor ($\Delta G^0 f = -50.88$ KJ/mole) |
| Seed | Palmitic Acid | Electron donor ($\Delta G^0 f = -305.0$ KJ/mole) |
| Seed | Stearic Acid | Electron donor ($\Delta G^0 f = -50.88$ KJ/mole) |
| Seed | Linoleic Acid | Electron donor ($\Delta G^0 f = -50.88$ KJ/mole) |
| Peel/Seed | Cu, Mn, Ni, Zn | Microelements for bacterial metabolism |
| Cull/Seed/Peel | Fe, Na, K, Ca | Macroelements for bacterial metabolism |
| Cull | Vitamin A, C | Growth factors for bacterial metabolism |

Microbial electrochemical systems (MESs) support an array of engineering applications including biosensors, electrolysis, desalination, reverse electrodialysis, and struvite production. The use of unprocessed solid organic wastes (SOWs) (e.g., food waste, sludge, soybean residue and rice husk, leaves, marine sediment, wheat straw as electron donors for MESs is conventionally known. Specifically, tomato pomace can serve as a viable electron donor in microbial fuel cells. There are a fair number of impedance studies on the use of pure substrates (e.g., lactate), wastewater, and marine wastes in MESs. However, there is a notable paucity in art relating to the impedance behavior of SOW-based MESs. Further, the art lacks a showing of MES studies that provide time-variant impedances characterizing the oxidation of unprocessed culled tomatoes. Therefore, a need exists to delineate the long-term oxidative behavior and impedance contributions of the particulate fraction (i.e., peel & seed) of the cull.

A series of DC techniques (voltammetry), AC techniques (electrochemical impedance analysis (EIS)), and spectrophotometry tests (chemical oxygen demand (COD)) can be used to compare the oxidative behavior of as is culled tomatoes with its peel and seed (P&S) and readily soluble substrates including pure dextrose (represent monosaccharides in the cull), pure acetate (fermentation product of dextrose), and municipal wastewater. Aspects of the present invention disclose indigenous redox shuttles (e.g. flavins) and dextrose-rich flesh in the cull promotes its oxidation, while the peel & seed in the cull impedes the degradation rates of culled tomatoes in MESs.

There are several reasons why oxidative behavior of unprocessed cull can be different from soluble substrates. First, the flesh in culled tomatoes serve an excellent source for energy-rich sucrose ($\Delta G0f=1551.8$ kJ/mole), amino acids ($\Delta G0f=763$ kJ/mole) and redox-active flavins (E'0FMN/FMNH2=−190 mV), all of which can promote the extracellular electron transport capabilities of ARB. The skin and seed in the culled tomatoes are rich in proteins, lipids, and micro- and macro-nutrients (Table 1).

Second, the peel and skin components of as is cull represent the complex particulate form of COD (pCOD) that is known for sluggish disintegration and hydrolysis in the biological systems. The MESs using the pCOD can be expected to suffer from the diffusion limitations. Third, unlike the municipal wastewater, the culled tomatoes possesses high carbohydrate content (39 mg/g cull), low pH, high electrical conductivity, and unique redox-active species (Table 1). From the large-scale treatment perspective, it is important to distinguish the electrical performance of cull-wastewater from municipal wastewater. Finally, the dextrose in the cull will proliferate the growth of methanogens. Based on the above background, it becomes important to distinguish the polarization response and impedance behavior of MESs with culled tomatoes from the peel & seed, fermentable (dextrose) and non-fermentable (acetate) substrates, and municipal wastewater.

At the typical low current densities (<10 A/m2) encountered in MESs, the present invention contemplates MESs with unprocessed cull outperforming the seed & skin and municipal wastewater. While counterintuitive, the cull is observed outperforming the pure chemicals (dextrose and acetate). Since the peel and seed are integral components of the cull, an EIS study can distinguish the temporal impedance contributions (charge transfer resistance, ohmic, and diffusion limitations) of the peel and skin to the electrochemical oxidation of culled tomatoes in MESs.

2. Materials & Methods

2.1. Reactor Configuration and Electrolyte Composition

A two-chambered microbial fuel cell as a laboratory model for microbial electrochemical systems (MESs) can be employed.
A hydrated Ultrex membrane provided a hydraulic separation between the anode and cathode chambers The 100 mM ferricyanide (in 50 mM phosphate buffer) can be used as the electron acceptor in the cathode. The tests can be carried out in five identical MESs varying in the type of carbon substrate 1) as is cull, 2) peel & seed, 3) dextrose, 4) acetate, and 5) municipal wastewater (Table 2). The five test MESs are herein referred as CULL, P&S, DEX, ACE, and WW. A MES that lacked carbon source can be run simultaneously to provide a control.

The anode can be inoculated with enriched mixture of electrochemically active microbial population described in our earlier study. In accordance with at least one evaluation, the performance of five test MESs in 14 consecutive cycles extended during 125 days of fed-batch operation. Planktonic microbes were eliminated at end of each cycle by draining the anolyte and gently washing the anode with 50 mM phosphate. The following minimal media can be used to prepare the anolyte: NH4Cl, 1.24 g/L; KCl, 0.52 g/L; NaH2PO4.H2O, 2.45 g L-1; Na2HPO47H2O, 4.576 g/L; vitamin mix, 10 ml/L; and trace minerals, 10 ml/L. The anolyte in test MESs can be obtained by modifying the minimal media with the carbon substrates (Table 2).

TABLE 2

Details of test and controls for MFCs.

|  |  | Electron Donor | Carbon Source | Electron Acceptor | Reference |
|---|---|---|---|---|---|
| Cull | 1. Polarization<br>2. Impedance<br>3. Voltammetry | Cull | Cull | Ferricyanide | Ag/AgCl |
| Seed & Skin | 1. Polarization<br>2. Impedance<br>3. Voltammetry | Seed &Skin | Seed &Skin | Ferricyanide | Ag/AgCl |
| Dextrose | 1. Polarization<br>2. Impedance<br>3. Voltammetry | Dextrose | Dextrose | Ferricyanide | Ag/AgCl |
| Acetate | 1. Polarization<br>2. Voltammetry | Acetate | Acetate | Ferricyanide | Ag/AgCl |
| Wastewater | 1. Polarization<br>2. Voltammetry | Chemical oxygen Demand | Wastewater | Ferricyanide | Ag/AgCl |
| Control | NA | None | None | Ferricyanide | Ag/AgCl |

2.1.1. CULL:

Fresh tomato culled tomatoes obtained, for example, from Immokalee farm, Naples, Fla., were quartered and boiled in distilled water for 5 minutes; cooled at 11 OC for 10 minutes; placed on an aluminum foil; heat-dried at 60 OC for 18 hours; and, 9.7 mg of powdered cull was mixed with one Liter of minimal media.

2.1.2. Peel & Seeds:

The cull, for example, was quartered and boiled in distilled water for 5 minutes and cooled at 11 OC for 10 minutes. The skin and seeds were manually separated from the dried cull and heated at 60 OC for 18 hours. The skin and seed were combined in a ratio of 3:4 (w/w) and mixed in minimal media to achieve 9.7 mg/L.

2.1.3. DEX, ACE, and WW.

The DEX and ACE used 1 g/L of dextrose and acetate respectively. The WW used primary clarifier effluent from Rapid City, S. Dak. wastewater treatment facility.

2.2. Analytical Methods, Data Acquisition & AC Impedance

In accordance with one exemplary method, 5 mL of anolyte can be periodically collected using a gastight syringe to measure its pH (Cole-Palmer probe) and sCOD (Method 5220 Hach COD system). Voltage data can be acquired with a DAQ/54 module configured with an external resistor. The polarization data can be obtained for test MESs on Day 1, 45, 59, 74, 86, and 105 by recording the steady state voltage values at a specified value of external resistor. The electrochemical impedance spectroscopy (EIS) for CULL, P&S, and DEX can be performed with CHI electrochemical workstation. The ACE and WW can be evaluated with Gamry600 workstation. The EIS tests can be performed at open circuit potential using an AC signal with an amplitude of ±10 mV and the EIS spectra was obtained in a frequency range of 10000 to 0.01 Hz. The EIS tests can use an anode as the working electrode and a cathode as counter and reference electrodes. The temporal EIS responses for CULL and P&S were recorded on Days 1, 16, 21, 45, 72, 88, 103, and 107. The solution resistance can be interpreted from the Nyquist plot as the real axis value at the high frequency intercept. The real axis value at low frequency intercept of Nyquist plot corresponds to the sum of the polarization resistance and the solution resistance.

2.3. Cyclic Voltammetry

A DC cyclic voltammetry technique can be used to analyze CULL, ACE, and WW using the anode as the working electrode, cathode as the counter electrode respectively, and Ag/AgCl system as a reference electrode. The working electrode can be scanned in a potential region of 0.8 and 0.8 V at a sweep rate of 10 mV/s. A Randles Sevcik equation can be used to analyze the cyclic voltammograms for CULL, ACE, and WW.

$$i_p = 0.4463 * n * F * A * C * \sqrt{\left(\frac{n * F * v * D}{R * T}\right)} \quad (1)$$

$$i_p = (2.687 * 10^5) * n^{\frac{3}{2}} * v^{\frac{1}{2}} * D^{\frac{1}{2}} * A * C \quad (2)$$

where
$i_p$=peak current (A); n=number of electrons transferred; A=electrode area (cm2);
F=Faraday Constant (C mole-1); D=diffusion coefficient of the species (cm2/s)
v=scan rate (V/s); C=bulk concentration of the species (mol/cm3); T=temperature (K)

3.0 Results and Discussion

Table 3 provides performance data for CULL, P&S, DEX, ACE, and WW.

TABLE 3

Exemplary experimental results.

| Test | Reactor | OCV (V) | Initial pH | Short Circuit Current (mA) | Peak Power density $mW/m^2$ | Peak Current density $mA/m^2$ | $R_s$ ($k\Omega \cdot cm^2$) | $R_p$ ($k\Omega \cdot cm^2$) |
|---|---|---|---|---|---|---|---|---|
| 1 | Cull | 0.743 | 7 | | 256 | 1504 | 2.4 | 12.49 |
| 2 | Seed &Skin | 0.737 | 7.1 | 2.37 | 132 | 456 | 3.27 | 17.02 |
| 3 | Dextrose | 0.79 | 7 | 5.09 | 169 | 927 | 3.22 | 30.7 |
| 4 | Acetate | 0.71 | 7.05 | 2.44 | 311 | 636.15 | 0.19 | 0.28 |
| 5 | Waste water | 0.29 | 7.09 | 1.66 | 143 | 431 | 0.10 | 6.74 |
| 4 | Control | 0.01 | 7 | | NA | NA | — | — |

Figure 1:
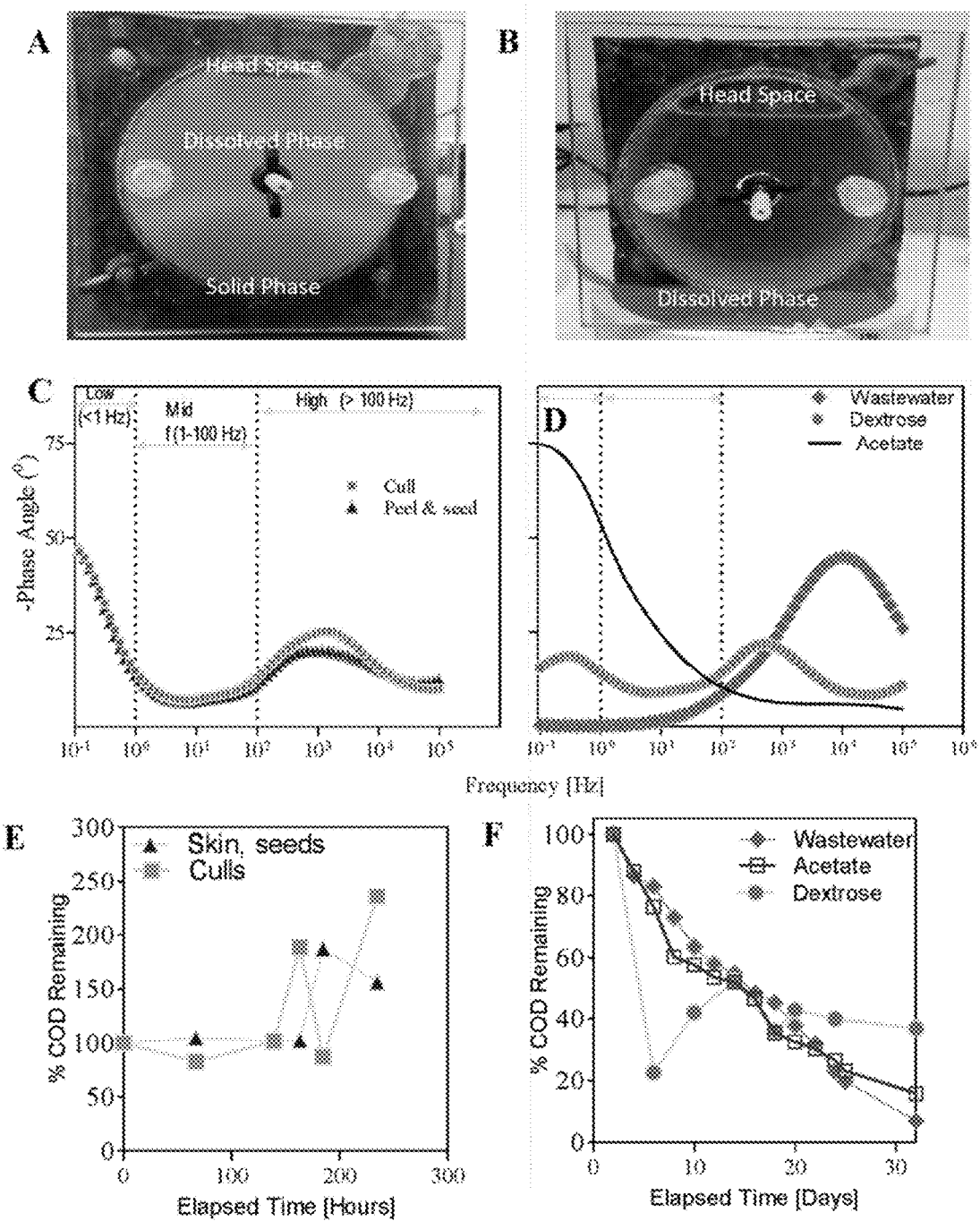
FIGS. 1(A)-(F) provide pictorial representations of (A) photograph of the anode compartment in CULL shows three distinct phases, i.e., solid, liquid, and gaseous phase; (B) photograph of the anode with readily soluble substrate (acetate in this case); (C) bode phase angle plot for as is cull and peel&seed in the anode; (D) bode phase angle plot for wastewater, dextrose, and acetate; (E) Chemical Oxygen Demand (sCOD) removal in MESs with solid substrates (cull and peel & seed); and (F) sCOD removal in MESs with wastewater, dextrose, and acetate (SD<5%; n=3) in accordance with illustrative aspects of the present disclosure.

3.1. Unique Oxidative Behavior of CULL and Peel & Seed Compared to Soluble Substrates FIGS. 1-6 demonstrates the unique oxidation behavior of the cull compared to the soluble substrates. Unlike the DEX, ACE, and WW (FIG. 1b), the CULL develops reddish-orange color due to the carotenoids (e.g., lycopene and redox-active β-carotene) it also promotes the formation of two distinct phases (FIG. 1a): i) the particulate phase (the peel & seed) characterized with pCOD and ii) a clear aqueous phase dominated by sCOD from the flesh (tissue, columella, pericarp, vascular bundle, and locular activity). Given the slow-kinetics of pCOD oxidation and the sluggish disintegration and hydrolysis reactions that characterize the P&S substrate, the inferior performance of P&S compared to CULL (FIGS. 1-5) is better understood. As expected, the DEX, ACE, and WW did not yield any color nor did the solid sludge (FIG. 1b). Data for FIG. 1(a)-(f) is obtained from MESs with biofilm age of roughly 100 days.

Additionally, both the CULL and P&S exhibited impedance behavior distinct from that of the DEX, ACE, and WW. The Bode phase angle plots for CULL and P&S yielded a phase angle maximum in the mid-to-low frequency region (LFR), indicating the presence of a charge transfer resistance (CTR) to the slow bio-electrochemical oxidation of pCOD (FIG. 1c). These LFR peaks did not appear in the DEX and ACE (FIG. 1d). The CULL and P&S also displayed time constants in the mid-frequency region (MFR) (FIG. 1c, 1d) that are likely indicative of the CTR to the indigenous redox shuttles (e.g. flavin and carotene; Table 1) in the cull and its peel and seed. These MFR peaks are also absent in the Bode plots for DEX, ACE, and WW.

Multiple relaxation constants (n>1) are observed in the Bode plots for CULL and P&S, while the ACE and WW yielded a single loop (FIG. 1). Contemporary EIS studies on the MESs with both waste water and pure substrates have reported only a single time constant. Finally, as expected, the temporal profiles for sCOD consumption in the ACE and WW (FIG. 1f) followed a linear pattern and demonstrated 92% sCOD removal (FIG. 10. However, the sCOD profiles for CULL and P&S follows a non-linear pattern (FIG. 1e). This is likely due to the complex dynamics of pCOD→sCOD conversion influenced by the synergistic effects of the disintegration and hydrolysis reactions, biofilm history, mass transfer limitations, and electrical parameters. Further, the sCOD initial for DEX, ACE, and WW can be manually adjusted to 1000 mg/L (FIG. 10; the different mass inputs of the CULL and P&S resulted in different sCODi values for CULL (2000 mg/L) and P&S (3000 mg/L) (FIG. 1d). The sCOD removal efficiency in the DEX was less than 50% and this is likely due to the fact that the dextrose can be fermented to sCOD-bearing organic acids and ethanol.

Figure 12:
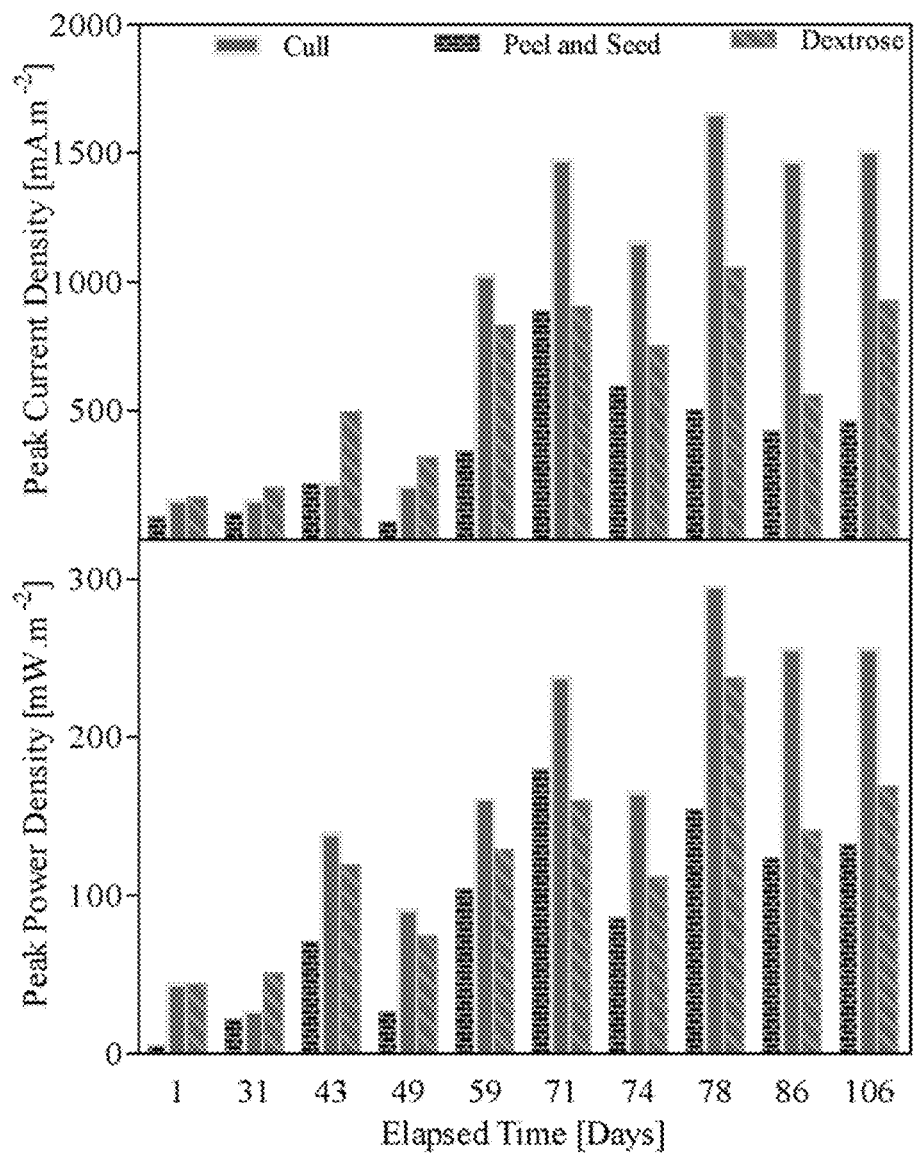
FIG. 12 provides pictorial representations of temporal changes in the power densities and current densities in three MFCs: i) cull, ii) peel and seed, and iii) dextrose in accordance with illustrative aspects of the present disclosure.

3.2. CULL Outperforms DEX, ACE-Defective Tomatoes Play Superior to Pure Chemicals The electrical performance of the P&S is shown to be inferior to CULL (FIG. 2b, 2c; FIG. 3) throughout the hundred days of operation (FIG. 12).

Ohms law is used to estimate the steady state electrical current under a load of 1000 ohm for FIGS. 2(A)-(F). Each cycle of fed-batch operation denotes 111 data points for externally measured voltage value. Similar start-up behavior is observed of MESs with soluble substrates (dextrose, acetate, and municipal wastewater), and solid substrates (culled tomatoes, peel & seed), both exhibited a lag phase, and the time requirements to achieve peak current density.

TABLE 4

Tabular results for one-way Anova test for OCV values for P&S, CULL, DEX.

| One-way analysis of variance | | | |
|---|---|---|---|
| P value | 0.2749 | | |
| P value summary | ns | | |
| Are means signif. different? (P < 0.05) | No | | |
| Number of groups | 3 | | |
| F | 1.318 | | |
| R squared | 0.04017 | | |
| Bartlett's test for equal variances | | | |
| Bartlett's statistic (corrected) | 0.9266 | | |
| P value | 0.6292 | | |
| P value summary | ns | | |
| Do the variances differ signif. (P < 0.05) | No | | |
| ANOVA Table | SS | df | MS |
| Treatment (between columns) | 0.007912 | 2 | 0.003956 |
| Residual (within columns) | 0.1891 | 63 | 0.003001 |
| Total | 0.1970 | 65 | |

While counter-intuitive, the CULL has outperformed DEX and ACE that used pure substrates (open circuit, FIG. 2a; closed-circuit, FIG. 2b-2f). The average OCVmax for CULL (0.71 V) is higher than P&S (0.67 V), DEX (0.7 V), ACE (0.63 V), and WW (0.41 V). Considering that P&S is characterized with the pCOD, it is observed that its OCV is equivalent to CULL and DEX. One-way ANOVA analysis confirms the absence of statistically significant differences between the mean OCV for CULL, P&S, and DEX (n=22; P-value=0.274>0.05, F=1.31; Bartlett's statistic=0.9266, p-value=0.629>0.05) (Tables 4-5). As anticipated, the OCV in the ACE is lower than DEX and higher than WW. FIGS.

Figure 2:
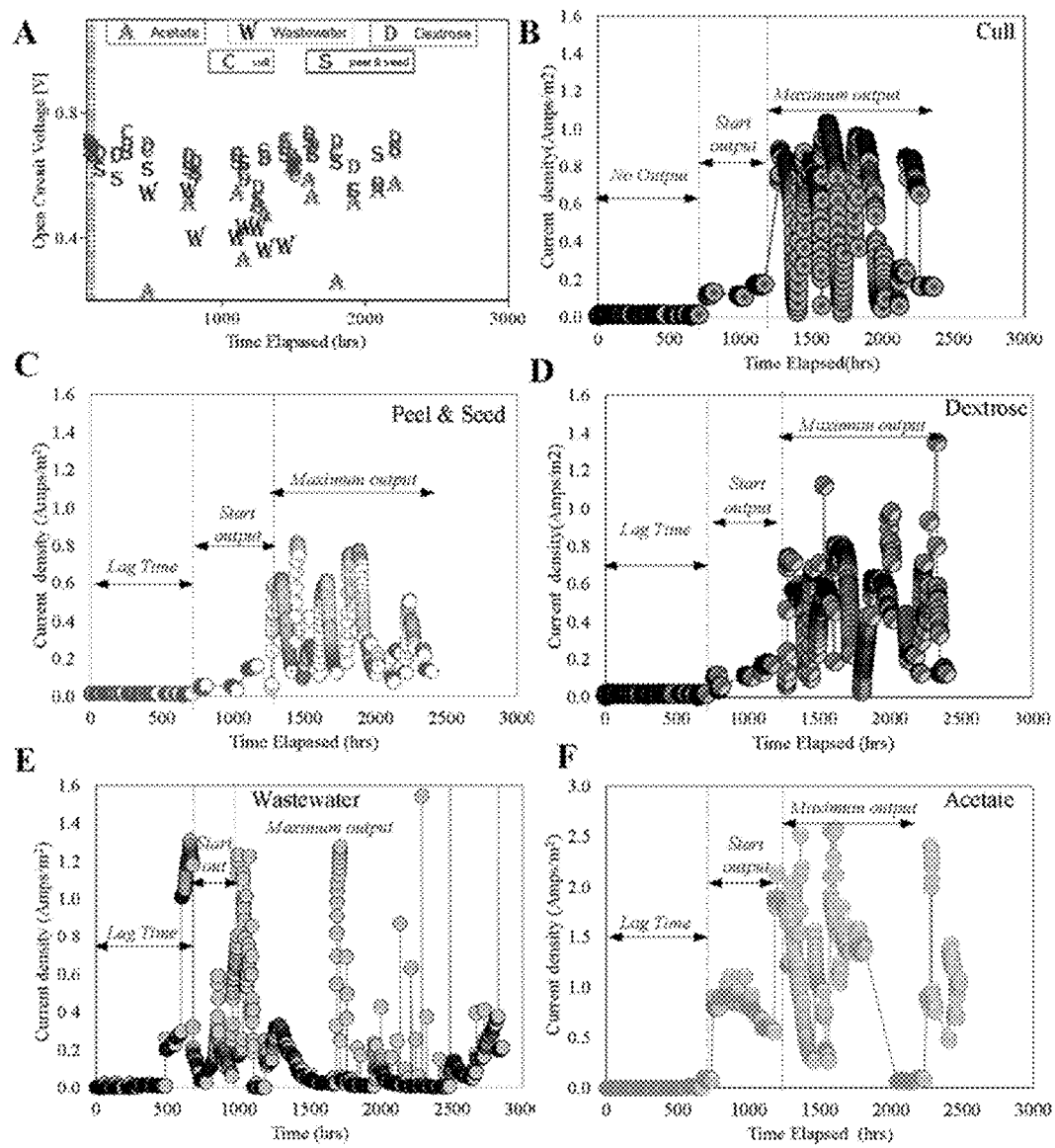
FIGS. 2(A)-(F) provide pictorial representations of (A) steady state OCV response during 3000 hours of continuous fed-batch operation; (B) steady state electrical performance as is cull under closed circuit; (C) steady state electrical performance of peel & seed; (D) steady state electrical performance of dextrose; (E) steady state electrical performance of municipal wastewater; and (F) electrical performance of acetate in accordance with illustrative aspects of the present disclosure.
Figure 3:
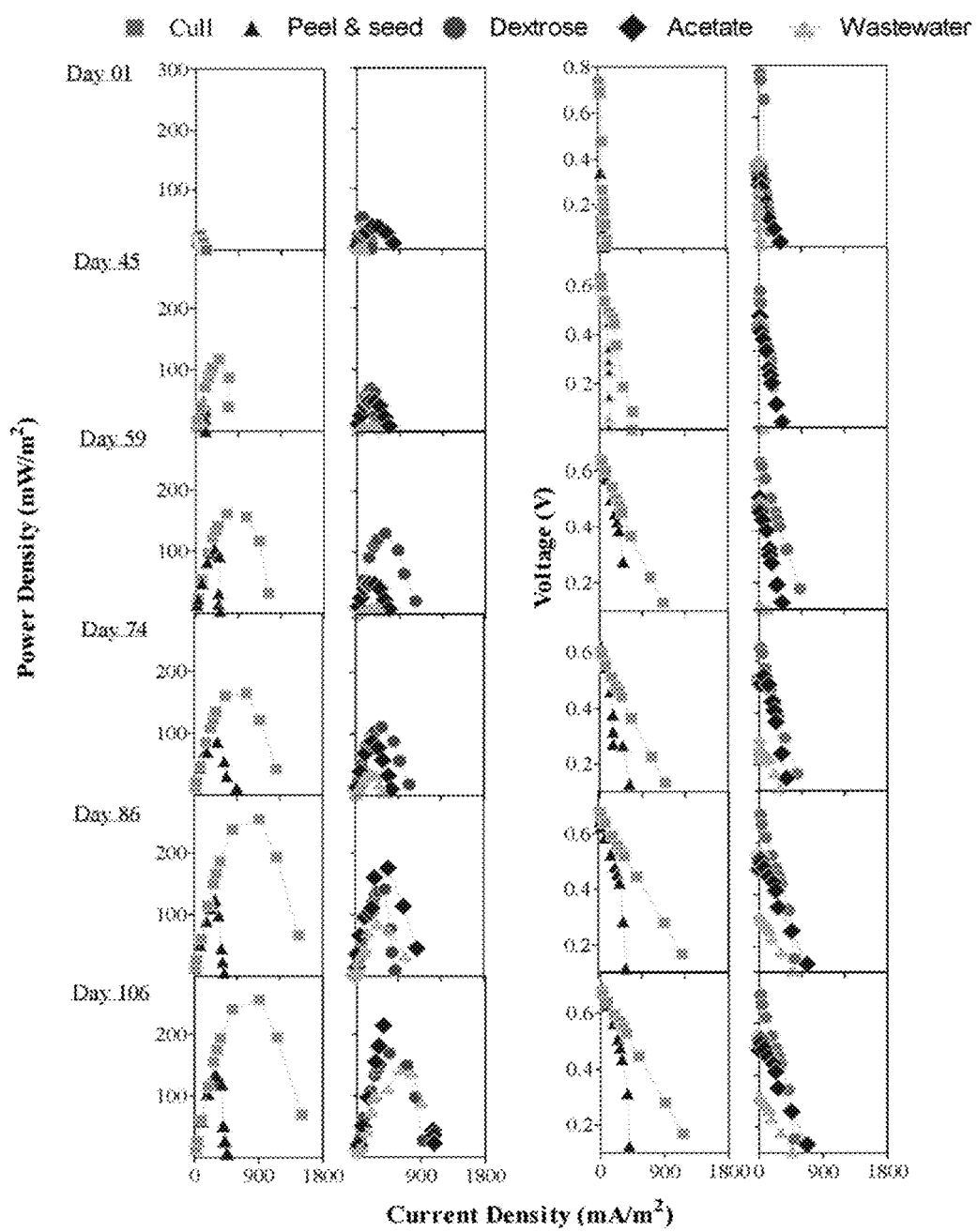
FIG. 3 provides pictorial representations of temporal data for power densities and polarization in MESs with as is solid substrates (culled tomatoes and peel & seed) and readily soluble substrates (dextrose, acetate and wastewater) in accordance with illustrative aspects of the present disclosure.
Figure 4:
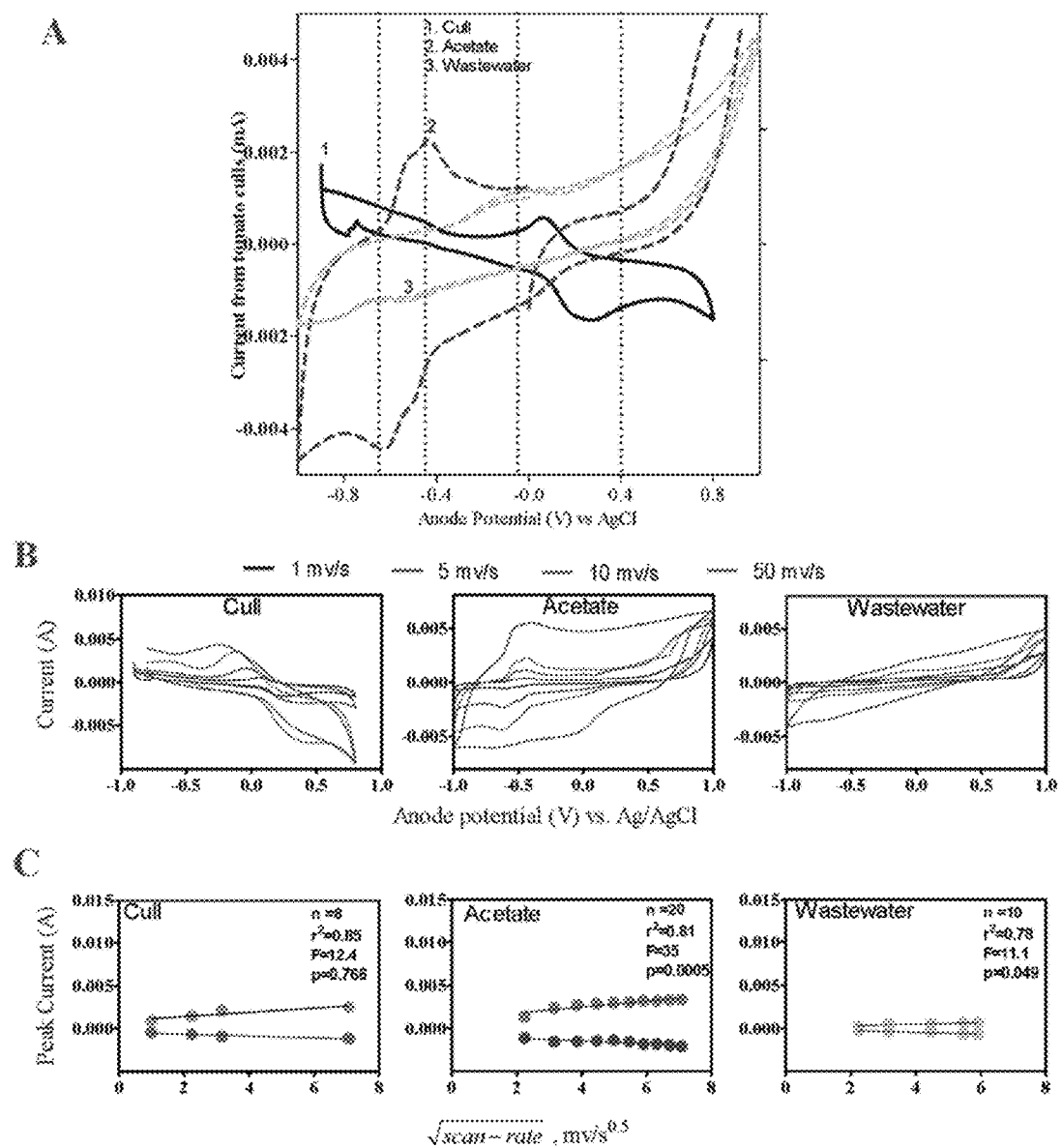
FIGS. 4(A)-(C) provide pictorial representations of A) cyclic voltammograms for as is culled tomatoes (blue solid line), acetate (purple dotted line), and soluble chemical oxygen demand in the municipal wastewater (dotted brown line); B) cyclic voltammograms with varying scan rates for three test MESs; and C) peak current against the square root of the scan rate for three test MESs (solid circles represent measured value and the solid line represents fitted data) in accordance with illustrative aspects of the present disclosure.

2(B)-2(F) indicate that the identical start-up behavior of five test MESs (2400 data points) under closed circuit conditions (load-1000Ω) and (FIG. 2).

TABLE 5

Column statistics for one-way Anova test for OCV values for P&S, CULL, DEX.

| Number of values | 22 | 22 | 22 |
|---|---|---|---|
| Minimum | 0.5210 | 0.5000 | 0.5600 |
| 25% Percentile | 0.6203 | 0.6343 | 0.6428 |
| Median | 0.6460 | 0.6705 | 0.6710 |
| 75% Percentile | 0.6725 | 0.6995 | 0.7040 |
| Maximum | 0.7430 | 0.7400 | 0.7710 |
| Mean | 0.6441 | 0.6604 | 0.6707 |
| Std. Deviation | 0.05006 | 0.06117 | 0.05249 |
| Std. Error | 0.01067 | 0.01304 | 0.01119 |
| Lower 95% CI | 0.6219 | 0.6333 | 0.6474 |
| Upper 95% CI | 0.6663 | 0.6875 | 0.6940 |

The CULL, P&S, and DEX exhibited a lag of 70 h to register minimal electrical output, and additional 700 h to register maximum current: CULL, 1.03 A/m2; P&S, 0.97 A/m2; and DEX, 0.98 A/m2 (FIG. 2). However, as shown in FIG. 3, the performance differences between the test MESs becomes more pronounced at higher current densities. Given the identical reactor configuration, the variance in polarization responses (FIG. 3) are attributed to the differences in the oxidation behavior of the carbon substrates. The polarization losses are ranked as: CULL<DEX<P&S<ACE<WW; the corresponding power densities are in the order: CULL>DEX>P&S>ACE>WW (FIG. 3). The polarization data for FIG. 3 is collected for representative cycles of fed-batch operation. The media replacements were performed on Days 12, 27, 43, 47, 53, 60, 67, 74, 84, 89, 95, and 103.

The bar plot in FIG. 12 compares the magnitude of power densities and current densities for CULL, P&S, and DEX. The CULL outperformed DEX during the fourteen different cycles (FIG. S3): the peak current density (1504 mA/m2) and power density (256.1 mW/m2) in CULL was 0.6 fold and 1.5 fold higher than DEX (FIG. 3). The superior performance of CULL is attributed to its monosaccharides (3 g sugar×g.cull-1), and the putative redox-active species, β-carotene characterized with high electron-transfer rates. The inferior performance of the DEX is attributed to methanogens that thrive in the glucose substrates and divert the electron flux towards reduced products (e.g., fatty acids). This observation is consistent with prior findings where glucose substrates yielded lower performance compared to the solid algae.

3.3. Redox Shuttles in CULL Appears at Potential of 0.3 V Higher than Contemporary Species The biofilm-coated anodes in both the CULL and ACE exhibited non-sigmoidal voltammograms indicating a single electron-transfer process. However, the CULL exhibits oxidation and reduction peaks at 0.255 V (vs. SHE) and 0.425 V (vs. SHE) respectively, and its midpoint peak potential (0.335 V vs. SHE) at higher values (more positive) compared to ACE (−0.34 V vs. SHE). The peak potential for the CV in the CULL was 0.3 V higher than that for MESs based on *Geobacter, R. palustris* DX-1, and *T. ferriacetica*. The higher-potential-redox-active-species (HPRAS) in the CULL dominated the CVs at all the tested scan rates (FIG. 4b). At low-scan rate, the ratio of cathodic and anodic peak current (ipc/ipa) in CULL was 1.56 indicating the quasi-reversible nature of the HPRAS that likely undergoes structural reorganization without disrupting its molecular structure. The peak potential of 0.33 V (vs. SHE) for HPRAS corresponds to the indigenous redox compounds in the culled tomatoes including quercetin (0.3 V vs. SHE) and carotenoid pigments (0.256-0.48 V vs. SHE).

Unlike CULL, the ACE exhibited redox peak at a lower voltage (−0.34 V vs SHE) corresponding to known electron acceptors such as ferredoxin (−0.398 Vs SHE) and cytochrome OmcB (−0.19 V vs SHE). For 1 mv/s scan rate, the ipc/ipa ratio for ACE is close to unity suggesting the reversible nature of participating redox-active species. This is a contemplated result, given the purity of the ACE compound compared with the complex particulate nature of the defective tomatoes in the CULL. The WW exhibited a mid-point peak at low potential (−0.19 V vs. SHE) whose peak current (ip) (both anodic and cathodic sweeps) is an order of magnitude lower than the CULL (FIG. 4a-c). The CVs shown in FIGS. 4(A)-(C) were generated after 365 days of fed-batch operation. Prior to obtaining CVs, the anolyte is totally drained, and washed with phosphate buffer two times.

The ipc/ipa ratio for both CULL and ACE decreased with increasing scan rates (FIG. 4b). The slow scan rate provides adequate time for redox-active species to participate in electrochemical reactions and contribute to higher faradic current (FIG. 4a). As scan rates grow faster and voltage range scanned wider, the diffusion rates decreased and the separation between the anodic and cathodic peak potentials (ΔEp) increases (FIG. 4b). The increase in ΔEp with increasing scan rate is attributed to the charge transfer limitations induced by the electrostatic factors, chemical interaction between electrolyte ions and anode and interactions of redox couples. The Randles-Sevcik equation (Eq. 1) can be used to confirm that the values of peak current (Ip) are directly proportional to the v½ (square root of scan rate) indicating the diffusion controlled current in both the CULL (n=8; r2=0.85; F=12.4; p=0.77) and ACE (n=20; r2=0.81; F=35; p=0.0005). However, the slope (0.00135) of the I-v½ curve in ACE is 27 fold higher than the CULL (slope=0.00005). The higher slope in the ACE indicates higher transfer coefficient of the participating redox-shuttles in the latter case. The differences in the slope can be attributed to the differences in the diffusion coefficient (D) of their respective redox couples. The easy electrocatalytic behavior of the redox shuttles and higher peak current (ip) in ACE can be explained by the fact that the biokinetic rate of the acetate oxidation is significantly higher than the pCOD oxidation in the CULL.

Figure 6:
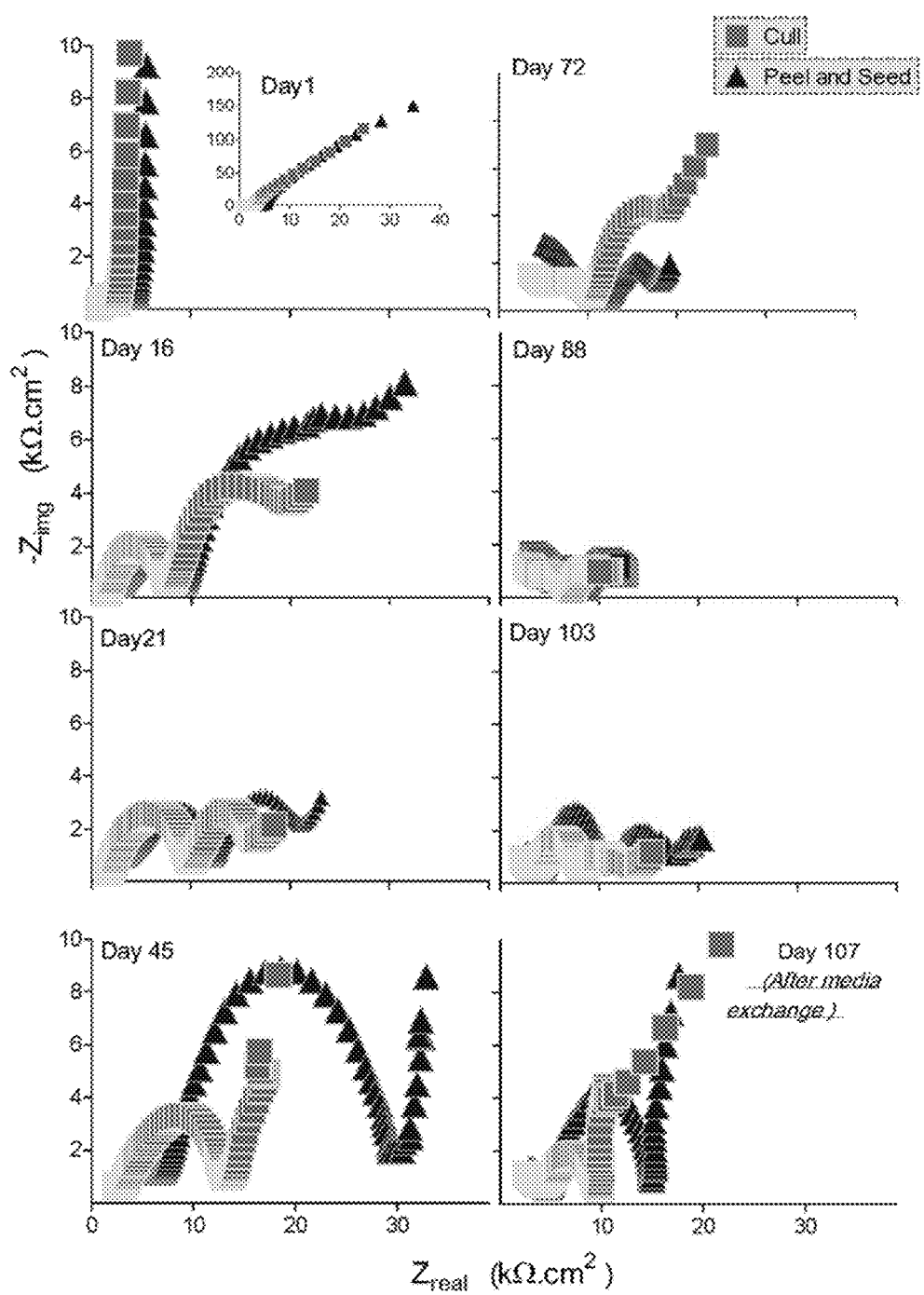
FIG. 6 provides pictorial representations of Nyquist responses for MES with peel and seed, and cull, for 100 days of fed-batch operation in accordance with illustrative aspects of the present disclosure.

3.4 the Higher Impedance in P&S Induces its Skewed Polarization Behavior at Higher Currents The P&S exhibits a skewed polarization behavior (i.e., concave-shaped power density curves) on Day 45, 59, and 74 (FIG. 3), while the CULL yields a smoother polarization response (FIG. 3). The recalcitrant behavior of the pCOD in the peel and seed limits the ability of P&S to meet the larger over potential required at higher current densities, while the readily available sCOD from the flesh sustains the performance of CULL at all the current densities. The long-term EIS studies have corroborated the dominant impedance behavior of the peel & seed at a range of frequencies (10 kHz-10 mHz) and time-scales (1-107 days) (FIG. 6). The frequency of the AC signal in FIG. 6 is varied from 10 kHz to 100 mHz with an amplitude of +10 mV. Impedance measurements for FIG. 6 are performed on a full cell configuration. The EIS plots of FIG. 6 are obtained during different cycles of fed-batch operation and reflects different biofilm history on the anode surface.

Figure 10:
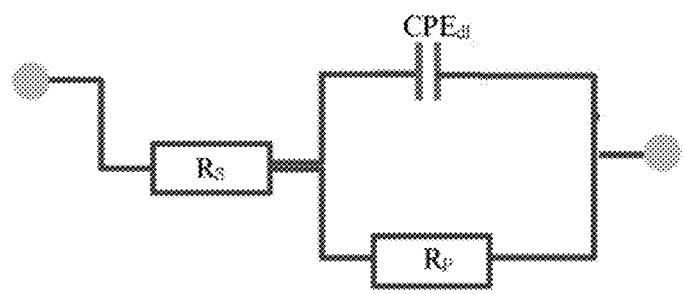
FIG. 10 provides a pictorial representation of a Randles circuit with elements representing solution resistance (Rs), polarization resistance (Rp), and double layer constant phase element (Cdl) in accordance with illustrative aspects of the present disclosure.
Figure 11:
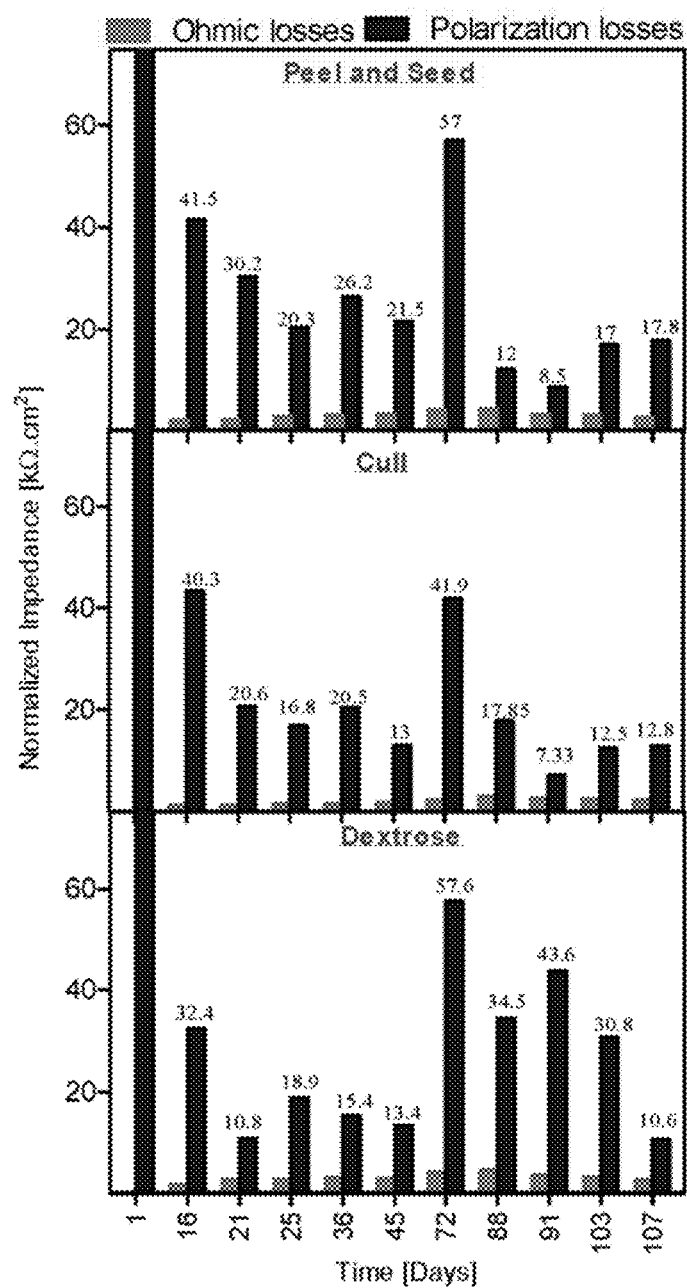
FIG. 11 provides pictorial representations of temporal changes in the normalized impedance for MESs with a) peel and seed, b) cull, and c) dextrose in accordance with illustrative aspects of the present disclosure.

The operational changes (e.g., media replacement) have resulted in the diverse impedance behavior of both the P&S and CULL (see the diverse shapes for the bell-shaped curves in the Nyquist plots; FIG. 6) throughout the 103 days of fed-batch operation. For instance, the Nyquist plots for Day 21 and Day 103 yielded three distinct loops; Day 16 and Day 72 yielded two incomplete semicircles; and the Day 45 and Day 107 yielded a single time constant but characterized with the diffusion resistance (extended arc in low-frequency region). It is therefore not feasible to identify a common model (e.g., Randle's circuit (FIG. 10)) that fits the entire range of the impedance data shown for 106 days (FIG. 6). FIG. 10 illustrates a Randle's circuit with elements representing solution resistance (Rs), polarization resistance ($R_p$), and double layer constant phase element ($C_{dl}$). Instead of using the electrical equivalent circuit fitting method, the polarization resistance (Rpolz) is observed as the real axis value at low frequency intercept. The Rpolz for the P&S is observed to be 17-39% greater than the CULL during all the time scales (FIG. 11). FIG. 11 shows the temporal changes in the normalized impedance for MESs with a) peel and seed, b) cull, and c) dextrose. For example, the Rpolz in the P&S is 1.7 fold higher than the CULL on day 45. The one-tailed t-test (95% confidence interval) confirms the statistically significant differences between the Rpolz for P&S and the CULL (paired test: p-value 0.0245; t=2.213; n=11; mean of difference=6.674, R2=0.3081). The EIS analysis indicates that the peel & seed will impede the oxidation of the culled tomatoes at higher current densities. No significant differences are observed in the Rohm in five test MESs (FIG. 6) (One-way ANOVA analysis; n=12; P-value=0.1375>0.05, F=2.109; Corrected Bartlett's statistic=1.647; p-value=0.439>0.05).

4.0 Exemplary Aspects of the Present Disclosure

The cyclic voltammetry (CV) tests confirm the electrochemical influence of mediators such as carotenoids, flavanoids and quercetins on oxidation of culled tomatoes in MESs. The CV tests show the peak potential of 0.33 V (vs. SHE) corresponding to quercetin compounds in tomatoes. The CV tests also show a peak that matches redox potential for carotenoids (0.204-0.449 V vs. SHE). Culled tomatoes contain a variety of redox-active species such as carotenoids, kampferol, malvin, myricetin, naringenin, naringin, petunidin, quercetin, and riboflavin, which qualify as redox-active mediators in MESs for following reasons; they are characterized by, at least: i) fast redox equilibration; ii) fully reversible reactions; iii) experimentally established standard redox potentials; and iv) defined stoichiometry with respect to number of electron and protons during faradaic processes. These mediators catalyze extracellular electron transfer from anode-respiring bacteria to solid electrodes in MESs and enhance their performance. The disclosure contemplates engineering strategies for mixing culled tomatoes with dilute wastewaters (e.g., municipal wastewater) and using the mixture to drive the MESs; for example, use the mixture to generate electricity in microbial fuel cells.

Figure 8:
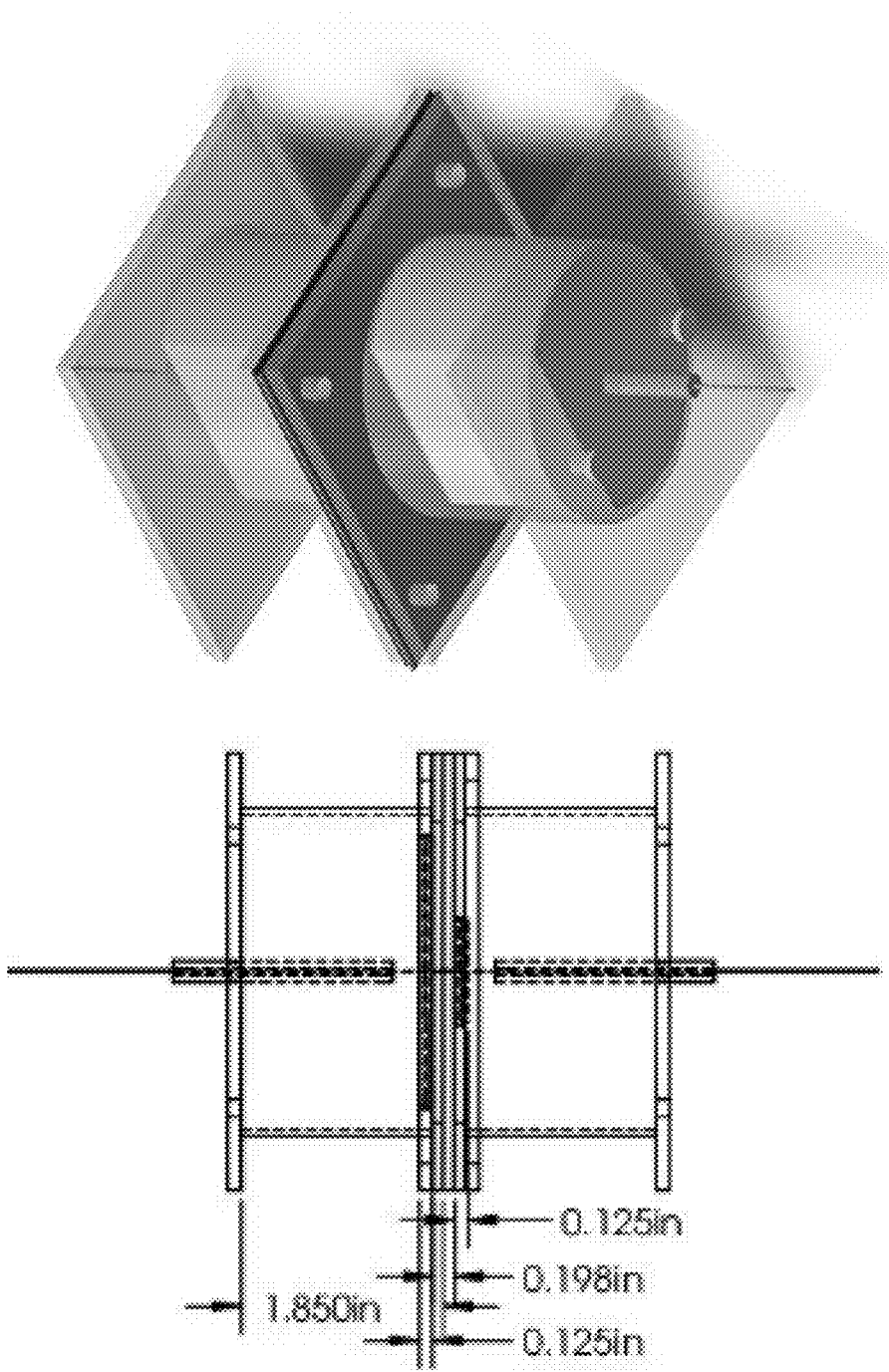
FIGS. 8(A)-(B) provide a pictorial schematic of a two-chambered microbial electrochemical system and contemplated technical specifications in accordance with illustrative aspects of the present disclosure.
Figure 9:
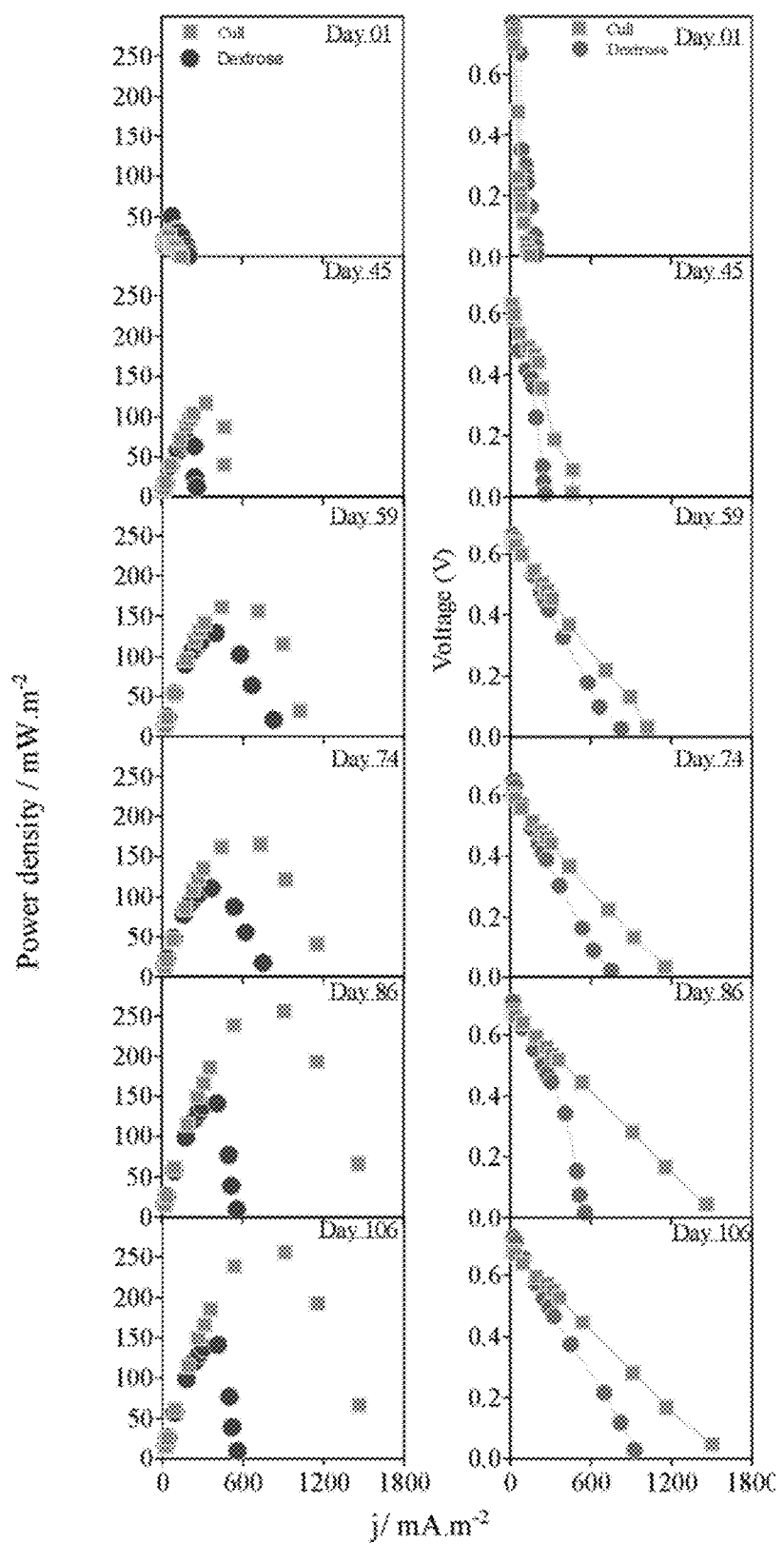
FIG. 9 provides pictorial representations of temporal data for electrochemical performance of culled tomatoes and dextrose in accordance with illustrative aspects of the present disclosure.

The type of bioreactor design (FIGS. 8(A)-(B)) used to build microbial electrochemical system (MES) influences the rate of electric current generated from oxidation of culled tomatoes and determines the overall performance of the MES. For example, the reactor design shown in FIG. 8 shows the schematic of two-chambered fuel cell fabricated with two acrylic blocks integrated with wing-nuts. The two blocks with identical geometry can be used to obtain anode and cathode compartments respectively. A polymer septum glued to the ports carried a titanium wire connected to the electrical circuitry. FIGS. 8(A)-(B) show some exemplary dimensions for inter-electrode spacing and membrane thickness. Each compartment can be further modified with an externally threaded joints to provide an inlet, outlet, and sampling ports. The anode and cathode compartments are physically separated with Ultrex membrane. Additionally, the bioreactor can be selected from reactors of the following type: (i) batch reactor, (ii) fed-batch reactor, (iii) continuous stirred tank reactor, (iv) granular sludge based upflow reactor, and (v) other reactor types. The MES with culled tomatoes can be configured in a galvanic mode: a microbial fuel cell for converting chemical energy of culled tomatoes into direct current (DC) electricity; a microbial desalination cell for using chemical energy of culled tomatoes to desalinate sea water; and a microbial capacitive deionization cell for using chemical energy of culled tomatoes to deionize brackish water. The MES with culled tomatoes can be configured in an electrolytic mode and use chemical energy of culled tomatoes to produce a variety of high-value products including methane, struvite and other reduced products.

The electrodes and membranes used in the MES can be based on a range of materials. For example, anode can be based on carbonaceous materials including nano-scale graphene, graphite felt, activated carbon, and reticulated vitreous carbon. The membranes can be based on anion exchange membranes or cation exchange membranes.

Contemporary MES designs do not use pure cultures due to contamination problems from microorganisms in feedstock. The defined composition of culled tomatoes and its year-around availability allows implementation of monocultures. A batch of culled tomatoes can be sterilized from a group of thermal, chemical, and radiation or filtration techniques. The sterilized batch can then be introduced to anode of MES prior to inoculation with monocultures of electricity generating bacteria from the classes of gamma proteobacteria, delta proteobacteria or firmicutes.

According to other exemplary aspects of the present disclosure, modification is achieved by use of monocultures of extremophiles (e.g., thermophilic bacteria including *Geobacillus* sp. strains DUSEL R7 and DUSEL 13). Monocultures can accelerate electricity generation from culled tomatoes. The thermophilic conditions can range from 60 to 120 degree centigrade.

The culled tomatoes in anode of MESs can be optimized to produce other valuable products microbially produced enzymes (e.g., cellulases, hydrolases, and lipolytic enzymes); pigments (e.g., carotenoids); proteins (e.g., globulin); and biopolymers.

According to some additional exemplary aspects of the present disclosure, the MES can be implemented virtually around the globe wherever there is culled tomatoes for the purpose of generating electricity from culled tomatoes or related wastes from tomato packing houses, tomato processing plants and other industrial facilities. The MES can also be used to generate electricity from tomato scraps typically available during long-term space missions including lunar missions.

5.0. Conclusions

Figure 5:
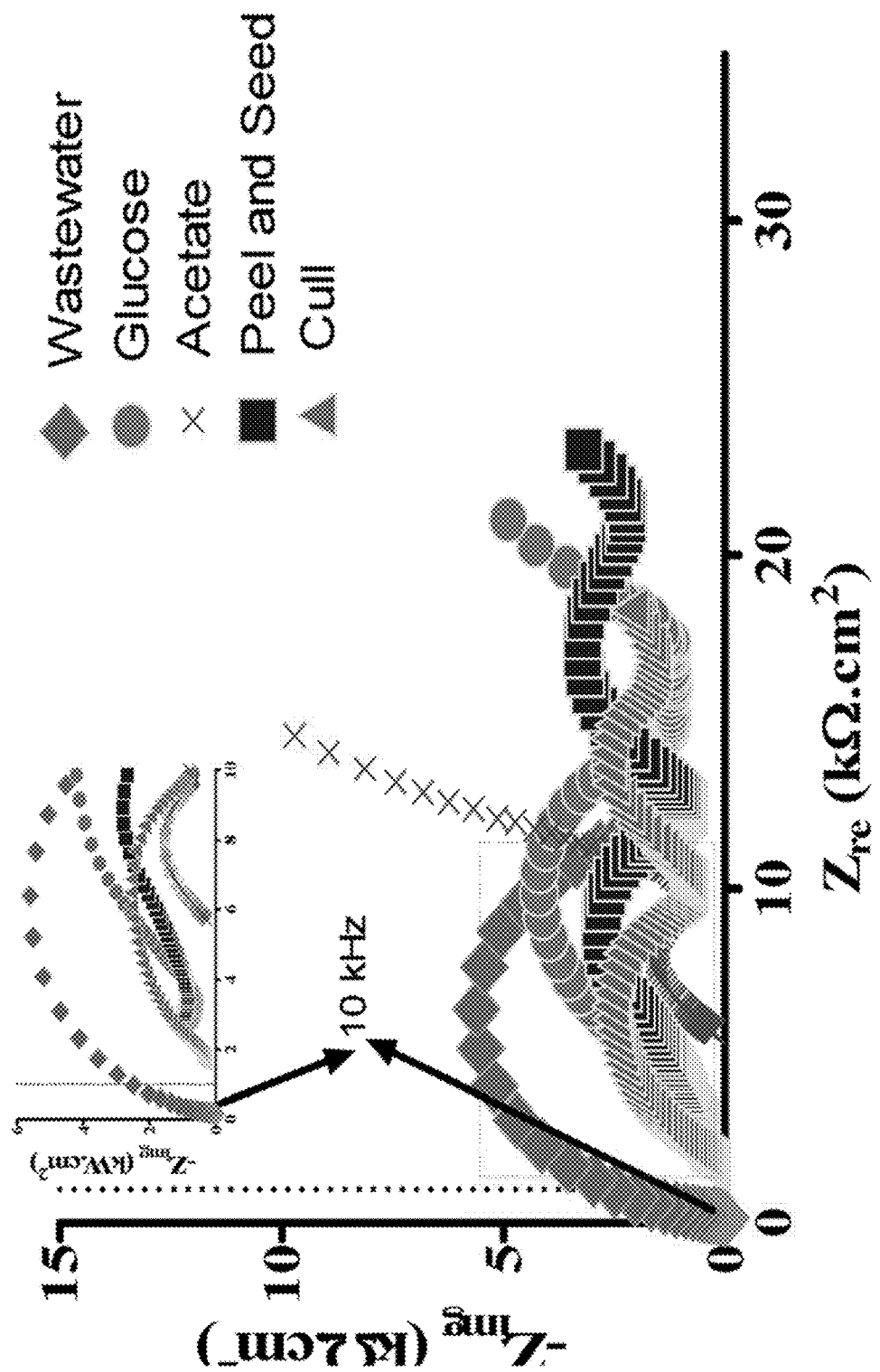
FIG. 5 provides pictorial representations of Nyquist plots for 100 days old MESs with wastewater (brown diamonds), glucose (red circles), acetate (X), peel & seed (blue squares), and as is solid culled tomatoes (green triangles) in accordance with illustrative aspects of the present disclosure.
Figure 13:
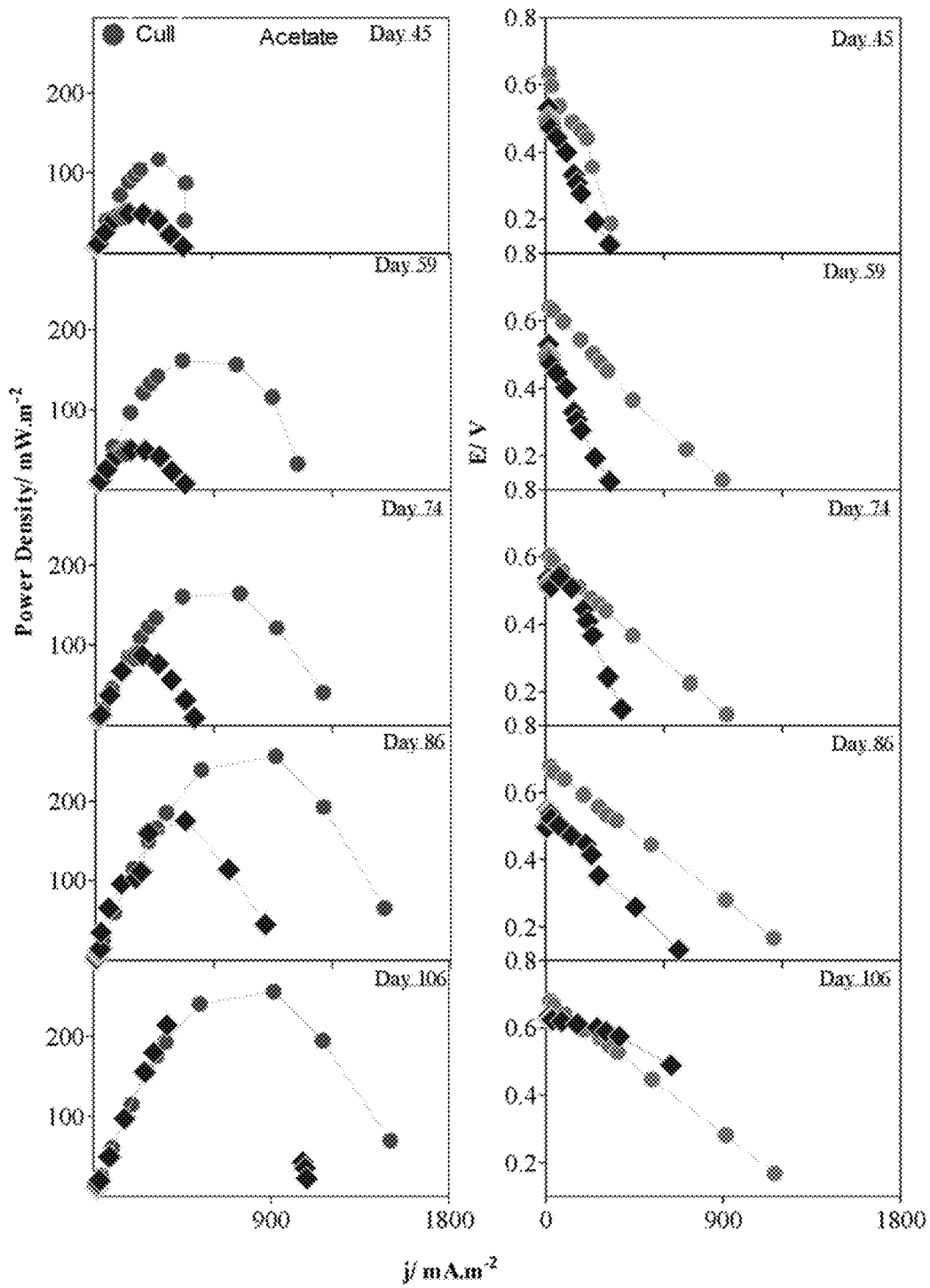
FIG. 13 provides pictorial representations of temporal data for electrochemical performance of culled tomatoes and acetate in accordance with illustrative aspects of the present disclosure.
Figure 14:
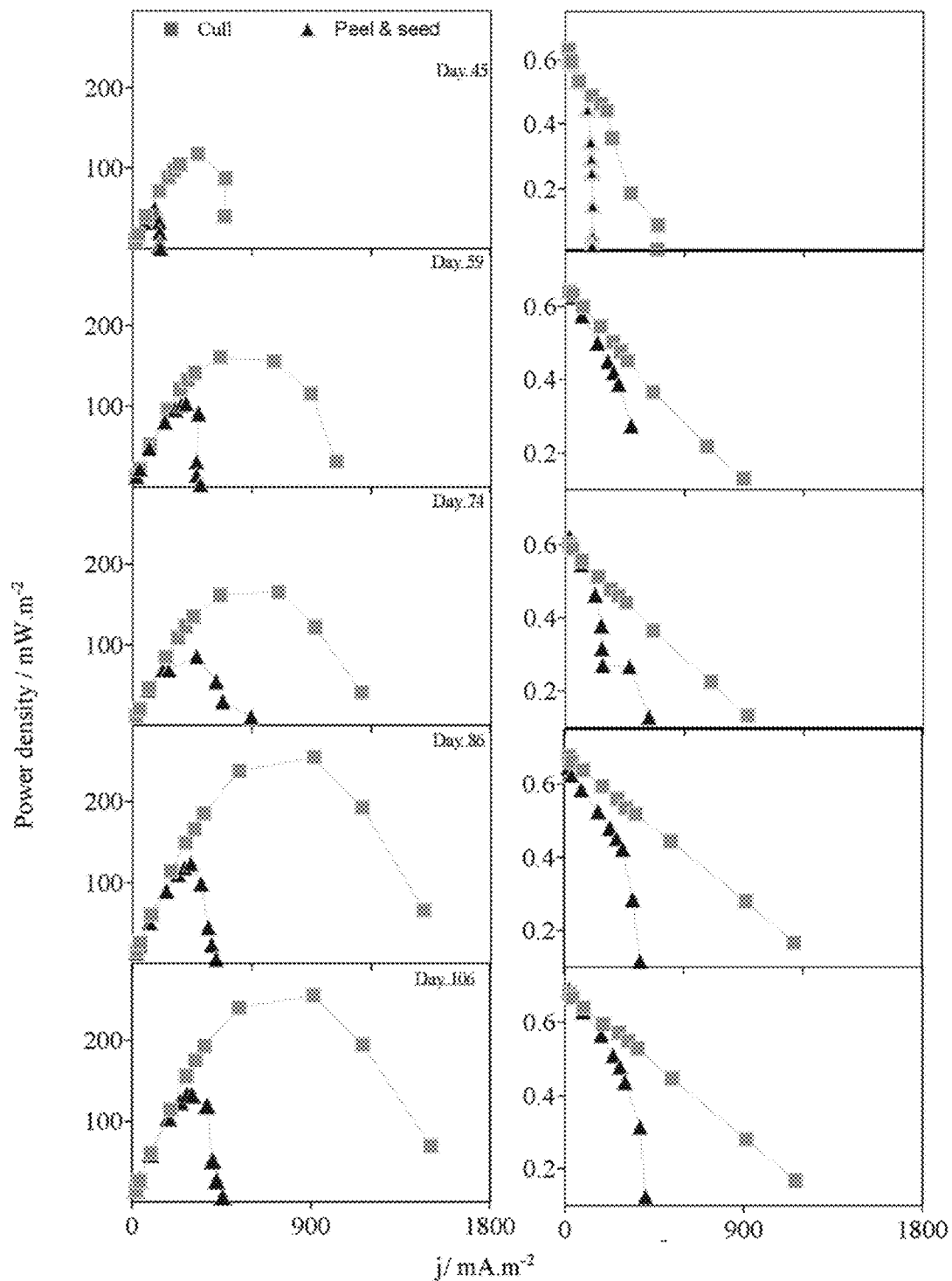
FIG. 14 provides pictorial representations of temporal data for electrochemical performance of culled tomatoes and peel & seed in accordance with illustrative aspects of the present disclosure.

The CULL offered high power density due to its low impedance compared to ACE and DEX (FIG. 5). The inset graph in FIG. 5 shows a clear view of the high frequency region represented by a dashed box. Both P&S and CULL achieved 88% reduction in the Rpolz within the 100 days of the fed-batch operation (FIG. 3; FIG. 6). The Rpolz in the CULL was at least 10-40% lower than the DEX (FIG. 11). Notably, the peak power densities (PPD) in the CULL are 1.5 fold higher than the DEX (FIG. 12 and FIG. 13) and 1.3 times higher than the ACE (FIG. 13). FIG. 12 shows the temporal changes in the power densities and current densities in three MFCs: i) cull, ii) peel and seed, and iii) dextrose. FIG. 13 shows the temporal data for electrochemical performance of culled tomatoes and acetate. Results contemplate impeded CULL performance as a result of the sluggish kinetics of pCOD from the peel & seed components (FIG. 14). FIG. 14 shows the temporal data for electrochemical performance of culled tomatoes and P&S. Further, both the P&S and CULL are sensitive to the media replacements, indicating their reliance on the non-bound redox mediators indigenous to the culled tomatoes.

The disclosure is not to be limited to the particular embodiments described herein. In particular, the disclosure contemplates numerous variations in the type of ways in which embodiments of the disclosure can be applied to providing and/or facilitating generation of electricity and other value-added products from culled tomatoes in microbially catalyzed electrochemical systems. The foregoing description has been presented for purposes of illustration and description. It is not intended to be an exhaustive list or limit any of the disclosure to the precise forms disclosed. It is contemplated that other alternatives or exemplary aspects that are considered included in the disclosure. The description is merely examples of embodiments, processes or methods of the disclosure. It is understood that any other modifications, substitutions, and/or additions can be made, which are within the intended spirit and scope of the disclosure. For the foregoing, it can be seen that the disclosure accomplishes at least all of the intended objectives.

The previous detailed description is of a small number of embodiments for implementing the disclosure and is not intended to be limiting in scope. The following claims set forth a number of the embodiments of the disclosure disclosed with greater particularity.

What is claimed is:

1. A method for generating electricity from matter derived from a tomato, the method comprising:
   providing a microbial electrochemical system comprising:
   a bioreactor having an anode chamber and a cathode chamber fabricated with two acrylic blocks integrated with a fastener, where the anode chamber and the cathode chamber are opposing electrodes connected to electrical circuitry;
   a membrane layer physically separating the opposing electrodes wherein the membrane layer comprises an anion exchange membrane or a cation exchange membrane;
   a flow pathway having an inlet and an outlet passing between the opposing electrodes; and
   a polymer septum located on the opposing electrodes carrying a titanium wire connected to the electrical circuitry;
   introducing tomato matter into the flow pathway of the microbial electrochemical system, wherein the tomato matter contains an anode-respiring bacteria; and
   catalyzing extracellular electron transfer from the anode-respiring bacteria of the tomato matter into the opposing electrodes in the microbial electrochemical system.

2. The method of claim 1 wherein the tomato matter comprises tissue, columella, pericarp, vascular bundle, and locular cavity.

3. The method of claim 1 wherein the tomato matter comprises at least tomato peel and tomato seed.

4. The method of claim 1 wherein the anode-respiring bacteria comprises a redox-active species.

5. The method of claim 1 wherein the redox-active species comprise carotenoids, kampferol, malvin, myricetin, naringenin, naringin, petunidin, quercetin, and riboflavin.

6. The method of claim 1 wherein the redox-active species are characterized by: i) a fast redox equilibration; ii) a fully reversible reaction; iii) standard redox potentials; and iv) a defined stoichiometry.

7. The method of claim 1 wherein the bioreactor comprises a batch reactor, a fed-batch reactor, a continuous stirred tank reactor, or a granular sludge based upflow reactor.

8. The method of claim 1 wherein the opposing electrodes comprise carbonaceous material.

9. The method of claim 1 further comprising:
   introducing monocultures of electricity generating bacteria into the tomato matter, wherein the monocultures comprise a gamma proteobacteria, a delta proteobacteria, or firmicutes.

10. The method of claim 1 further comprising:
    introducing monocultures of electricity generating bacteria into the tomato matter, wherein the monocultures comprise extremophiles.

11. The method of claim 1 further comprising: optimizing the tomato matter to produce at least one of:
    (i) microbially produced enzymes;
    (ii) pigments;
    (iii) proteins;
    (iv) biopolymers.

12. A microbial electrochemical system for generating electricity from matter derived from a tomato, the system comprising:
    a bioreactor having an anode chamber and a cathode chamber fabricated from acrylic blocks with identical geometry, where the anode chamber and the cathode camber are with opposing electrodes connected to electrical circuitry;
    a hydrated membrane layer separating the anode chamber from the cathode chamber, where the membrane is hydrated with ferricyanide with a phosphate buffer;
    a flow pathway having an inlet and an outlet passing between the opposing electrodes; and
    a polymer septum located on the opposing electrodes carrying a titanium wire connected to the electrical circuitry;
    wherein the tomato matter containing an anode-respiring bacteria is introduced into the flow pathway of the microbial electrochemical system;
    wherein the tomato matter further comprises one or more monocultures of electricity generating bacteria, wherein the monocultures comprise extremophiles; and
    wherein extracellular electron transfer is catalyzed from the anode-respiring bacteria of the tomato matter into the opposing electrodes in the microbial electrochemical system for generating electricity.

13. The system of claim 12 wherein the tomato matter comprises tissue, columella, pericarp, vascular bundle, and locular cavity.

14. The system of claim 12 wherein the tomato matter comprises at least tomato peel and tomato seed.

15. A galvanic circuit for using chemical energy from tomato matter, comprising:
    a microbial electrochemical device with electrical circuitry comprising:

a bioreactor having opposing electrodes formed of an anode chamber and a cathode camber fabricated from two acrylic blocks of identical geometry where the opposing electrodes are electrically coupled to the electrical circuitry;

a hydrated membrane separating the anode chamber and the cathode chamber, where the membrane is an electron acceptor hydrated with 100 mM ferricyanide with 50 mM phosphate buffer and providing separation between the anode chamber and the cathode chamber;

a flow pathway having an inlet and an outlet passing between the opposing electrodes; and a polymer septum glued to ports supporting a titanium wire coupling the electrical circuitry with the anode chamber and the cathode chamber;

one or more controls operably configured with the electrical circuitry to ascertain one or more outputs for polarization, impedance and voltammetry of the microbial electrochemical device;

wherein the tomato matter containing an anode-respiring bacteria is introduced into the flow pathway of the microbial electrochemical device;

wherein the microbial electrochemical device comprises a microbial desalination cell for using the chemical energy of the tomato matter to desalinate sea water; and wherein extracellular electron transfer is catalyzed from the anode-respiring bacteria of the tomato matter by the microbial electrochemical device.

16. The galvanic circuit of claim 15 wherein the microbial electrochemical device comprises a microbial capacitive deionization cell for using the chemical energy of the tomato matter to deionize brackish water.

* * * * *

UNITED STATES PATENT AND TRADEMARK OFFICE
CERTIFICATE OF CORRECTION

| | | |
|---|---|---|
| PATENT NO. | : 10,388,977 B2 | Page 1 of 1 |
| APPLICATION NO. | : 15/476768 | |
| DATED | : August 20, 2019 | |
| INVENTOR(S) | : Venkataramana Gadhamshetty, Namita Shrestha and Alex Fogg | |

It is certified that error appears in the above-identified patent and that said Letters Patent is hereby corrected as shown below:

In the Claims

Column 16, Claim 12, Line 39 delete "with"

Column 16, Claim 12, Line 39 change "camber" to --chamber--

Column 17, Claim 15, Line 2 change "camber" to --chamber--

Signed and Sealed this
First Day of October, 2019

Andrei Iancu
*Director of the United States Patent and Trademark Office*

UNITED STATES PATENT AND TRADEMARK OFFICE
CERTIFICATE OF CORRECTION

Page 1 of 1

PATENT NO. : 10,388,977 B2
APPLICATION NO. : 15/476768
DATED : August 20, 2019
INVENTOR(S) : Venkataramana Gadhamshetty, Namita Shrestha and Alex Fogg It is certified that error appears in the above-identified patent and that said Letters Patent is hereby corrected as shown below:

On the Title Page

Item (73) In the Assignee, change "FLORIDA GULF COAST UNIVERSITY BOARD OS TRUSTEES" to --FLORIDA GULF COAST UNIVERSITY BOARD OF TRUSTEES--

Signed and Sealed this
Thirteenth Day of April, 2021

Drew Hirshfeld
*Performing the Functions and Duties of the*
*Under Secretary of Commerce for Intellectual Property and*
*Director of the United States Patent and Trademark Office*